(12) United States Patent
Niwa et al.

(10) Patent No.: US 8,267,996 B2
(45) Date of Patent: Sep. 18, 2012

(54) INTRAOCULAR LENS

(75) Inventors: Kazuharu Niwa, Nagoya (JP); Yutaka Kumazawa, Nagoya (JP); Atsushi Kobayashi, Seto (JP)

(73) Assignee: Kowa Company, Ltd. (JP)

( * ) Notice: Subject to any disclaimer, the term of this patent is extended or adjusted under 35 U.S.C. 154(b) by 39 days.

(21) Appl. No.: 11/912,499

(22) PCT Filed: May 20, 2005

(86) PCT No.: PCT/JP2005/009278
§ 371 (c)(1),
(2), (4) Date: Oct. 24, 2007

(87) PCT Pub. No.: WO2006/123427
PCT Pub. Date: Nov. 23, 2006

(65) Prior Publication Data
US 2009/0030514 A1    Jan. 29, 2009

(51) Int. Cl.
*A61F 2/16* (2006.01)
(52) U.S. Cl. ............ 623/6.16; 623/6.54; 623/6.46
(58) Field of Classification Search ........ 623/6.18–6.21, 623/6.38–6.49, 6.11
See application file for complete search history.

(56) References Cited

U.S. PATENT DOCUMENTS

| | | |
|---|---|---|
| 4,244,060 A | 1/1981 | Hoffer |
| 4,343,050 A | 8/1982 | Kelman |
| 4,588,405 A | 5/1986 | Knolle, Jr. |
| 4,661,109 A | 4/1987 | White |
| 4,718,905 A | 1/1988 | Freeman |
| 4,808,181 A | 2/1989 | Kelman |
| 4,961,746 A | 10/1990 | Lim et al. |
| 5,071,432 A | 12/1991 | Baikoff |
| 5,074,942 A | 12/1991 | Kerns |
| 5,476,513 A * | 12/1995 | Brady et al. ............ 623/6.4 |
| 5,716,403 A | 2/1998 | Tran et al. |
| 6,110,202 A * | 8/2000 | Barraquer et al. ....... 623/6.43 |
| 6,129,759 A | 10/2000 | Chambers |

(Continued)

FOREIGN PATENT DOCUMENTS

EP    0346245 A1    12/1989

(Continued)

OTHER PUBLICATIONS

Search Report issued in PCT/JP2005/009278, mailed Jun. 28, 2005.

(Continued)

*Primary Examiner* — David H Willse
*Assistant Examiner* — Tiffany Shipmon
(74) *Attorney, Agent, or Firm* — Rossi, Kimms & McDowell LLP

(57) ABSTRACT

An intraocularlens of novel structure by which the outer circumferential part of an optical portion can be pressed stably against a posterior capsule under worn state and crisis of secondary cataract can be suppressed more advantageously. A pair of coupling portions (14, 14) are formed to hold an optical portion (12) between them in one direction perpendicular to the optical axis, wherein the outer fringe parts of the coupling portions (14, 14) are made thicker than the outer fringe part of the optical portion (12), a pair of supporting portions (16, 16) are formed to project from the outer fringe parts of the coupling portions (14, 14) and a edge contour part (32) is formed continuously on the outer fringe parts of the optical portion (12) and respective posterior surfaces (20, 24) of the coupling portions (14, 14) so as to extend smoothly along the entire circumference thereof.

15 Claims, 23 Drawing Sheets

U.S. PATENT DOCUMENTS

| | | | |
|---|---|---|---|
| 6,140,438 | A | 10/2000 | Ojio et al. |
| 6,926,744 | B1 | 8/2005 | Bos et al. |
| 2002/0026241 | A1 | 2/2002 | Baikoff |
| 2002/0095212 | A1* | 7/2002 | Boehm .................. 623/6.37 |
| 2002/0138140 | A1 | 9/2002 | Hanna |
| 2003/0078655 | A1 | 4/2003 | Callahan et al. |
| 2003/0120342 | A1 | 6/2003 | Green |
| 2004/0024454 | A1* | 2/2004 | Toop ....................... 623/6.4 |
| 2005/0187621 | A1* | 8/2005 | Brady ...................... 623/6.16 |
| 2006/0122700 | A1 | 6/2006 | Kurosaka et al. |
| 2009/0082861 | A1 | 3/2009 | Marunaka et al. |

FOREIGN PATENT DOCUMENTS

| | | | |
|---|---|---|---|
| EP | 0363213 | A2 | 4/1990 |
| EP | 0904747 | A2 | 3/1999 |
| EP | 1358858 | A1 | 11/2003 |
| GB | 2171912 | A | 9/1986 |
| JP | 02-156943 | A | 6/1990 |
| JP | 9-508810 | A | 9/1997 |
| JP | 10-024097 | A | 1/1998 |
| JP | 11-056998 | A | 3/1999 |
| JP | 11-70130 | A | 3/1999 |
| JP | 2001-269358 | A | 10/2001 |
| JP | 2001-525219 | A | 12/2001 |
| JP | 2003-504115 | A | 2/2003 |
| JP | 2003-190193 | A | 7/2003 |
| JP | 2003-522592 | A | 7/2003 |
| JP | 3494946 | B2 | 11/2003 |
| WO | 9513022 | A1 | 5/1995 |
| WO | 0069370 | A1 | 11/2000 |
| WO | 0128458 | A1 | 4/2001 |
| WO | 0164135 | A1 | 9/2001 |
| WO | 03/055416 | A1 | 7/2003 |
| WO | 2004/096099 | A1 | 11/2004 |

OTHER PUBLICATIONS

International Search Report issued in application No. PCT/JP2005/009281, dated Jun. 28, 2005, which is the foreign counterpoart of related co-pending U.S. Appl. No. 11/914,605.

International Preliminary Report issued in application No. PCT/JP2005/009281, dated Dec. 26, 2007 which is the foreign counterpart of related co-pending U.S. Appl. No. 11/914,605.

International Preliminary Report issued in application No. PCT/JP2005/009281, dated Dec. 6, 2007, which is the foreign counterpart of related co-pending U.S. Appl. No. 11/914,605.

Supplemental Search Report issued in corresponding European application No. 05741635.6-2320/1882461, dated Dec. 1, 2009.

Supplemental Search Report issued in corresponding European appl No. 05744110.7, dated Dec. 3, 2009 which corresponds to U.S. Appl. No. 11/914,605.

English translation of the International Preliminary Report issued in corresponding application No. PCT/ JP2005/009278, mailed Dec. 6, 2007.

* cited by examiner ary complication of cataract treatment. A secondary cataract is a subsequent complication that arises due to proliferation of epithelial cells within the capsule from which the lens of the eye has been removed, resulting in clouding of the posterior capsule within the optical zone of the intraocular lens.

INTRAOCULAR LENS

This application is a U.S. National Phase Application of PCT International Application PCT/JP2005/009278 (published as WO 2006/123427) having an international filing date of May 20, 2005. The disclosure of the PCT application is incorporated herein by reference.

TECHNICAL FIELD

The present invention relates in general to an intraocular lens of one-piece design in which the optical portion and the supporting portions are integrally formed; and relates in particular to an intraocular lens able to effectively inhibit secondary cataracts.

BACKGROUND ART

One well-known method used in the past for treating the ocular disorder known as a cataract involves removing the lens of the eye, and employing an intraocular lens as a substitute for the lens. An intraocular lens of this kind is used by being inserted into the capsule from which the lens has been removed. The lens has an optical portion, which functions in place of the lens of the eye, and a support portion for positioning and immobilizing the optical portion within the capsule.

In the area of cataract treatment, there have been numerous improvements in relation to intraocular lens design and surgical techniques for the purpose of reducing demands on patient imposed by surgery and for avoiding subsequent complications. However, even now, it cannot be said that the probability of subsequent complications is low. Secondary cataracts are known to occur with high frequency as a subsequent complication of cataract treatment. A secondary cataract is a subsequent complication that arises due to proliferation of epithelial cells within the capsule from which the lens of the eye has been removed, resulting in clouding of the posterior capsule within the optical zone of the intraocular lens.

Various research has been carried out for the purpose of preventing such secondary cataracts, and one outcome of this research has been to elucidate that rates of incidence of secondary cataracts will differ depending inter alia upon the shape of the intraocular lens. Specifically, it has been shown that by maintaining the outer fringe portions of an intraocular lens so that they are pressed against the posterior capsule, infiltration of epithelial cells into the optical zone can be blocked, making it possible to inhibit the incidence of secondary cataracts.

Another recent development has been the proposal of intraocular lenses of one-piece design, in which the optical portion and the supporting portions are integrally constituted using the same material. Such one-piece type intraocular lenses are beginning to attract attention for reasons such as the fact that they are easier to manufacture than conventional intraocular lens of three-piece type in which, after forming pair of supporting portions separate from the optical portion, these supporting portions are affixed to the optical portion.

However, for reasons relating to design, intraocular lens of one-piece type have the problem that, as compared with intraocular lenses of conventional three-piece design, it is more difficult to keep the outer fringe portions of the lens securely pressed along its entire circumference against the posterior capsule during wear. Therefore, an inherent problem is that it will be more difficult to inhibit secondary cataracts, as compared with intraocular lenses of the conventional three-piece design.

Specifically, in the edge contour constituting the line of intersection of the posterior surface and the outside edge surface of the optical portion of an intraocular lens of conventional three-piece design, a distinct continuous edge part is formed along the entire circumference. Thus, by pressing this edge part against the posterior capsule, it is a simple matter to maintain the outer fringe part of the optical portion securely and stably in contact along its entire circumference against the posterior capsule. In an intraocular lens of one-piece type, however, the supporting portions are formed projecting with generally unchanging thickness dimension from the outer fringe part of the optical portion. Thus, in the areas where the supporting portions are formed, no edge contours are present at the outer fringe part of the optical portion. It is therefore exceedingly difficult to keep the optical portion pressed firmly against the posterior capsule in the areas where the supporting portions are formed, and as a result epithelial cells can easily infiltrate through these areas, reducing the effectiveness in inhibiting secondary cataracts.

Intraocular lenses of one-piece type for addressing this problem have been proposed in Patent Document 1 (WO/2004/096099A1) and Patent Document 2 (JP-A 2003-504115).

According to the intraocular lens taught in the former Patent Document 1, the thickness dimension of the supporting portions formed projecting out from the outer circumferential surface of the optical portion is designed to be smaller than the thickness dimension of the outer circumferential surface of the optical portion and is disposed with bias towards the anterior surface of the optical portion, thereby forming an edge-shaped edge contour around the entire circumference of the back edge of the outer circumferential surface of optical portion.

However, in the intraocular lens of the design taught in Patent Document 1, the thickness dimension of the supporting portions will inevitably be smaller than the thickness dimension of the outside edge surface of the optical portion. Thus, it will be difficult to achieve sufficient strength of the supporting portions, and due to insufficient strength in the supporting portions it will be difficult to maintain shape stability and positioning stability during wear; moreover, there will be a risk of insufficient pressing force of the edge contour against the posterior capsule, which is derived from the action of force transmitted through the supporting portions. Furthermore, it will be necessary to increase the thickness dimension of the optical portion in order to ensure strength of the supporting portions, creating the problem of greater imposition on the patient due to the fact that the incision wound made in the capsule during surgery must be made larger, in order to accommodate the thicker optical portion.

The intraocular lens disclosed in the latter Patent Document 2 is designed so that the supporting portions formed projecting from the optical portion are thick at the basal end only, thus forming on the posterior surface of the supporting portion a shoulder portion situated at a location in proximity to the optical portion; this shoulder portion is utilized to constitute an edge contour at locations where the supporting portions are formed. According to the design disclosed in Patent Document 2, by forming the supporting portions so as to project on a slope towards the anterior side, it is possible to avoid making the supporting portions thinner, while at the same time forming a shoulder portion on the posterior surface of the supporting portions in their medial section.

However, since the shoulder portion is formed on the back face of the supporting portions in the medial section in their direction of projection, the shoulder portion will connect the two widthwise edges of the supporting portions at either edge across their width, in a generally orthogonal geometry. Thus the edge contour, which has been formed utilizing the posterior surface of the supporting portions from the outer fringe part of the optical portion, will have a generally right-angled inflection point. When the edge contour is pressed against the posterior capsule, the presence of such an inflection point will tend to produce in the posterior capsule irregular wrinkle-like deformation centered around the inflection point. There is a risk that due to this irregular deformation, the surface of the posterior capsule will fail to follow the shape of the edge contour that has been formed in the outer fringe part of the back faces of the optical portion and the supporting portions, creating a gap or the like. Additionally, since the posterior capsule is not only flexible but also of spherical shape, and since the inflection point is positioned furthest towards the fringe, the inflection point may catch on the posterior capsule and produce a gap between the edge contour and the posterior capsule, at a location lying towards the center from the location pressed against by the inflection point.

Patent Document 1: WO2004/096099A1
Patent Document 2: JP-A 2003-504115

DISCLOSURE OF THE INVENTION

Problem the Invention Attempts to Solve

With the foregoing in view, it is an object of the present invention to provide an intraocular lens of novel structure whereby the outer circumferential part of the optical portion can be pressed stably against the posterior capsule about the entire circumference during wear, thereby more advantageously inhibiting the onset of a secondary cataract.

Means for Solving the Problem

The modes of the present invention with a view to addressing this problem will be described hereinbelow. The various constitutional elements employing in the modes set forth herein may be employed in all possible combinations. The modes and technical features of the present invention are not limited the disclosure herein and should be understood on the basis of the specification in its entirety and the accompanying drawings, as well as on the basis of inventive concepts that will be apparent to the practitioner of the art based on the disclosure herein.

Specifically, a first mode of the present invention provides an intraocular lens of one-piece type wherein an optical portion of generally circular shape in front view and constituted including a lens zone having prescribed optical characteristics, are integrally formed with supporting portions that extend radially outwardly from the optical portion, and with the lens inserted in an eye, are disposed in contact against an inside surface of an outer circumferential part of a capsule thereby holding the optical portion positioned pressed against the inside surface of the capsule on a retinal side thereof, and an edge contour of edge shape is formed surrounding the optical portion at a back face of the optical portion in a direction of an optical axis thereof and pressed against the inside surface of the retinal side of the capsule, the intraocular lens being characterized in that: a pair of coupling portions that respectively spread outwardly in a diametrical direction from the outer circumferential part of the optical portion at locations situated in opposition along one direction across a diameter thereof are formed with circumferential length greater than the supporting portions; the supporting portions are formed projecting out from outer fringe parts of the coupling portions, with a thickness dimension at each outer fringe part of the coupling portion from which the supporting portion projects out being greater than a thickness dimension at an outer fringe part of the optical portion; at the outer fringe part of the coupling portion in a coupling section thereof with the supporting portion, the coupling portion projects further towards the back face side than the supporting portion so that the outer fringe parts of the optical portion and the posterior surfaces of the pair of coupling portions cooperate to form the edge contour that extends continuously about an entire circumference so as to surround the optical portion, and the edge contour is formed to have a shape extending smoothly along the entire circumference in a circumferential direction.

In the intraocular lens of structure according to the present mode, the edge contour is formed through cooperation of the optical portion and the coupling portions and extends continuously around the entire circumference so as to surround the optical portion, with a shape that extends smoothly around the entire circumference in the circumferential direction, whereby infiltration of epithelial cells into the optical zone of the optical portion can be effectively prevented, and a reduced rate of onset of secondary cataracts can be achieved.

Specifically, with a conventional structure like that disclosed in JP-A 2003-504115, the edge contour includes an inflection point in the circumferential direction. When the edge contour is pressed against the inside surface of the capsule when the intraocular lens is implanted within the capsule, it will produce concentration of stress in the area of the capsule inside surface that is pressed by the inflection point part, causing wrinkling or other irregular deformation in the inside surface of the flexible capsule. Therefore the edge contour will not be maintained in sufficiently intimate contact against the capsule inside surface and it will be difficult to effectively prevent infiltration of epithelial cells into the optical zone. On the other hand, with the intraocular lens of structure according to the present mode in particular, the edge contour extending in the circumferential direction is formed with a smooth continuous shape around the entire circumference in the circumferential direction, and therefore the edge contour does not include an inflection point but rather has a gently bowing shape overall, making it difficult for stress concentrations to be produced at any particular location of the edge contour when pressed against the inside surface of the capsule. For this reason, with the intraocular lens of structure according to the present mode, during wear the inside surface of the posterior capsule will not experience any irregular deformation at its flexible, spherical bowing face due to contact by the edge contour; and the entire circumference of the edge contour will be stably pressed against the inside surface capsule, advantageously creating a condition of intimate contact. Consequently, it will be possible through contact of the edge contour against the capsule inside surface to more effectively prevent infiltration of propagating epithelial cells into the portion of the posterior capsule situated in the optical zone of the optical portion, and to advantageously achieve secondary cataract-inhibiting effect.

Additionally, the pair of supporting portions are connected to the optical portion via the pair of coupling portions. In addition, the thickness dimension at the outer fringe part of the coupling portions from which the supporting portions project is greater than the thickness dimension at locations at the outer fringe part of the optical portion further away from the coupling portions. For this reason, when the edge contour is formed, there is a higher degree of freedom with regard to establishing the thickness of the supporting portions, as compared to where the supporting portions are projected directly out from the outer fringe part of the optical portion. Consequently, it is possible to avoid thinning of the supporting portions at their basal portion and to assure sufficient strength on the part of the supporting portions; and the intraocular lens can be stably positioned and immobilized within the capsule, as well as more advantageously achieving pressing force of the edge contour against the capsule inside face.

A second mode of the invention provides an intraocular lens according to the first mode, wherein the edge contour along the entire circumference thereof in the circumferential direction is either linear or gibbous-curving towards an outside circumference.

In the intraocular lens of structure according to the present mode, the edge contour is disposed in more stable intimate contact against the spherical bowing surface of the posterior capsule, and the effect of reducing the incidence of secondary cataracts can be more advantageously achieved. Specifically, by forming the edge contour with shape along the entire circumference in the circumferential direction that is either linear or convexly curved towards the outside circumference, the edge contour will come into contact over a wider area with the inside face of the spherical bowing surface of the posterior capsule. For this reason, stress or strain created by contact of the intraocular lens with the capsule inside face can be dispersed over a wider area of the capsule, and a condition of stable intimate contact can be maintained by avoiding concentration of stress or strain at a particular location.

A third mode of the present invention provides an intraocular lens according to the first or second mode, wherein the edge contour about the entire circumference thereof is positioned in a given plane extending generally orthogonal to a center axis of the optical portion.

In the intraocular lens of structure according to the present mode, the edge contour is positioned within the same plane about its entire circumference, whereby a generally equal level of pressing force is directed onto the spherical bowing surface of the posterior capsule about the entire circumference of the edge contour, creating a condition of generally uniform contact by the edge contour along its entire circumference, as well as avoiding irregular deformation of the capsule due to concentration of pressing force in a particular location. Thus, a condition of intimate contact of the edge contour against the capsule inside face can be advantageously assured.

A fourth mode of the present invention provides an intraocular lens according to any of the first to third modes wherein posterior surfaces of the coupling portions are generally flat surfaces extending in a generally orthogonal direction to the center axis of the optical portion, and anterior surfaces of the coupling portions are sloping surfaces which projects gradually towards an anterior surface side moving further away towards an outer fringe side from the optical portion.

In the intraocular lens of structure according to the present mode, by constituting the posterior surfaces of the coupling portions as generally flat surfaces which extend in the generally orthogonal direction to the center axis of the optical portion, the edge contour will be positioned about its entire circumference in the same plane extending orthogonal to the center axis of the optical portion. For this reason, condition of generally unchanging, stable intimate contact can be achieved about the entire circumference, and irregular deformation of the capsule can be prevented, ensuring a state of intimate contact of the edge contour against the capsule. Moreover, by constituting the anterior surfaces of the coupling portions as sloping surfaces which project gradually towards the anterior surface side moving in the diametrical direction towards the outer fringe side away from the optical portion, the coupling portions gradually become thicker towards the outer fringe side, and there is a high degree of freedom with regard to establishing the thickness of the supporting portions which project from the outer fringe part of the coupling portions.

A fifth mode of the present invention provides an intraocular lens according to the first or second mode, wherein the posterior surfaces of the coupling portions are sloping surfaces which project gradually towards the posterior surface side moving further away towards an outer fringe side from the optical portion; anterior surfaces of the coupling portions are sloping surfaces which project gradually towards the anterior surface side moving further away towards the outer fringe side from the optical portion; and the anterior surfaces of the coupling portions have a larger slope angle than the posterior surfaces of the coupling portions.

In the intraocular lens of structure according to the present mode, by constituting the posterior surfaces of the coupling portions as sloping surfaces which project gradually towards the posterior surface side moving towards the outer fringe side, a higher level of pressing force of the edge contour against the capsule inside surface can be achieved, and the edge contour can be advantageously disposed in intimate contact against the capsule inside surface. In particular, by employing such a sloping surface for the posterior surface, the edge contour can be easily endowed with an acute angle cross section that directs pressing force in a more focused manner, making it possible to more advantageously achieve a condition of intimate contact. Moreover, by making the slope angle of the posterior surface smaller than the slope angle of the anterior surface, sufficient thickness on the part of the supporting portions can be assured, without the need for the coupling portion outer fringe parts to project with excessive height towards the posterior surface side. For this reason, while advantageously achieving a condition of intimate contact against the posterior capsule by means of the acute angle formed in the edge contour, the edge contour will not project to any significant extent towards the posterior surface side with respect to the location of the posterior surface of the optical portion. Therefore, a condition of intimate contact of the optical portion posterior surface against the posterior capsule can be effectively achieved, and intimate contact against the posterior capsule can be effectively achieved at the posterior surface side of the intraocular lens.

A sixth mode of the present invention provides an intraocular lens according to any of the first to fifth modes wherein the thickness dimension at a basal portion of the supporting portions projecting out from the coupling portions is equal to or greater than the thickness dimension at locations away from portions where the coupling portions are formed at the outer fringe part of the optical portion.

In the intraocular lens of structure according to the present mode, buckling or other irregular deformation caused by concentration of stress during wear can be more advantageously prevented from occurring in connecting segments between the coupling portions and the supporting portions. Furthermore, reaction force of contact produced by contact of the supporting portions against the capsule will be efficiently transmitted to the edge contour, making it possible to consistently direct an adequate level of pressing force thereon.

A seventh mode of the present invention provides an intraocular lens according to any of the first to sixth modes wherein a thickness dimension of the outer fringe part of the optical portion is generally unchanging along the entire circumference, including those areas where the coupling portions are formed and other areas away from those areas where the coupling portions are formed.

In the intraocular lens of structure according to the present mode, it is possible to prevent problems such as optical distortion of the optical portion. Moreover, due to the presence of the coupling portions, it is possible to establish the thickness dimension at the basal portion of the supporting portions in a manner unconstrained by the thickness dimension of the optical portion at its outer fringe part.

An eighth mode of the present invention provides an intraocular lens according to any of the first to seventh modes wherein, in the outer fringe part of the pair of coupling portions and the outer fringe part of the optical portion which constitute the edge contour, the outer circumferential surface which rises from the edge contour constitutes an axial surface that extends around the entire circumference thereof in a direction generally parallel to the center axis of the optical portion.

In the intraocular lens of structure according to the present mode, the outer circumferential surface which rises from the edge contour constitutes an axial surface that extends generally parallel to the center axis of the optical portion, whereby it is possible to advantageously form an edge shape of the edge contour which is formed by cooperation by the outer fringe parts of the posterior surface sides of the optical portion and the pair of coupling portions.

A ninth mode of the present invention provides an intraocular lens according to any of the first to eighth modes wherein the edge contour has an acute angle cross section in at least a portion thereof.

The intraocular lens of structure according to the present mode is adapted to focus contact force against the capsule, and can achieve more stable contact of the edge contour against the capsule inside surface.

A tenth mode of the present invention provides an intraocular lens according to any of the first to ninth modes wherein the outer fringe part of the coupling portion is composed of an arcuate distal end outer fringe part with an outer circumferential face of arcuate shape disposed concentrically with the center axis of the optical portion, and bilaterally disposed fringe portions for smoothly connecting respective circumferential edge portions of the arcuate distal end fringe part to the outer fringe part of the optical portion; and wherein a width dimension of the supporting portions is smaller than the circumferential length of the arcuate distal end fringe part, with the supporting portion formed projecting from a circumferential center portion of the arcuate distal end fringe part.

With the intraocular lens of structure according to the present mode, it is possible to more easily manufacture the intraocular lens pertaining to the present invention. Specifically, in the cutting process (lase cutting method), control of the cutting operation is easier owing to the fact that the circumferential shapes of the outer fringe parts of the optical portion and the coupling portions are all concentric arcs, thus making it possible to execute cutting with a high degree of accuracy. Meanwhile, in the molding process, it will be possible to reduce or avoid internal stress and residual strain caused by shrinkage during polymerization.

An eleventh mode provides an intraocular lens according to any of the first to tenth modes wherein each of the pair of supporting portions projects extending out in a direction generally orthogonal to the center axis of the optical portion; and a center point of the supporting portion in a thickness direction thereof is positioned with bias towards the anterior surface of the optical portion, in relation to the center point of the thickness direction of the optical portion.

In the intraocular lens of structure according to the present mode, the supporting portions are formed so as to extend in a direction generally orthogonal to the center axis of the optical portion, without having to be sloped, while at the same time being able to advantageously achieve pressing force of the edge contour against the inside surface of the capsule. Specifically, whereas conventional practice was to form the supporting portions so that their projecting distal ends slope gradually towards the anterior surface; by means of this slope, components of the contact reaction force against the capsule which is transmitted to the optical portion via the supporting portions are directed in such a way as to induce displacement of the optical portion towards the posterior surface side. In the intraocular lens pertaining to the present mode, however, the center of the supporting portion in its thickness direction biased towards the anterior surface side with respect to the center of the optical portion in its thickness direction, whereby despite the fact that the supporting portions project extending out in a direction generally orthogonal to the center axis of the optical portion, the reaction force of contact against the posterior capsule, which force is transmitted to the optical portion via the supporting portions, will be transmitted with bias axially forward with respect to the center point of the thickness of the optical portion. For this reason, strain caused by the transmitted contact reaction force, and consequently a force component thereof, will induce displacement of the optical portion so as to press it against the capsule inside wall situated on the back face side thereof, and effective pressing force will be attained in the edge contour. Moreover, by forming the supporting portions so as to extend in a direction generally orthogonal to the center axis of the optical portion, the intraocular lens will be much easier to manufacture than in the case where sloped supporting portions must be formed; and in the case of manufacture by a cutting process, a smaller axial dimension can be established in the lens blank, thereby improving the yield of the lens material and reducing production costs.

A twelfth mode of the invention provides an intraocular lens according to any of the first to eleventh modes, wherein the lens is integrally formed of soft material that is foldable or rollable.

In the intraocular lens of structure according to the present mode, even in an intraocular lens formed of soft material tending to have problems in terms of strength of the supporting portions in particular, it will be possible nevertheless to advantageously achieve strength of the supporting portions, and to attain stable positioning of the optical portion by the supporting portions, and intimate contact of the edge contour against the capsule inside surface. Moreover, by forming the lens from soft material, the coupling portions will easily deform in response to the spherical bowing inside surface shape of the capsule; and the edge contour situated on the outer fringe part of the posterior surface side of the coupling portions which are positioned further outward in the optical portion axis-perpendicular direction from the edge contour situated on the outer fringe part of the posterior surface side of the optical portion, will be disposed in more stable contact against the capsule inside surface, whereby intimate contact of the edge contour against the capsule can be improved.

Effect of the Invention

As will be apparent from the preceding description, according to the intraocular lens of one-piece design of structure in accordance with the present invention, with the intraocular lens inserted into the eye, the edge contour which surrounds the entire circumference of the optical portion will be pressed stably along its entire circumference against the posterior capsule, thereby advantageously avoiding migration of epithelial cells into the optical zone. For this reason, secondary cataracts caused by infiltration and clouding in the optical zone by epithelial cells can be effectively inhibited.

EXPLANATION OF NUMERALS

Figure 1:
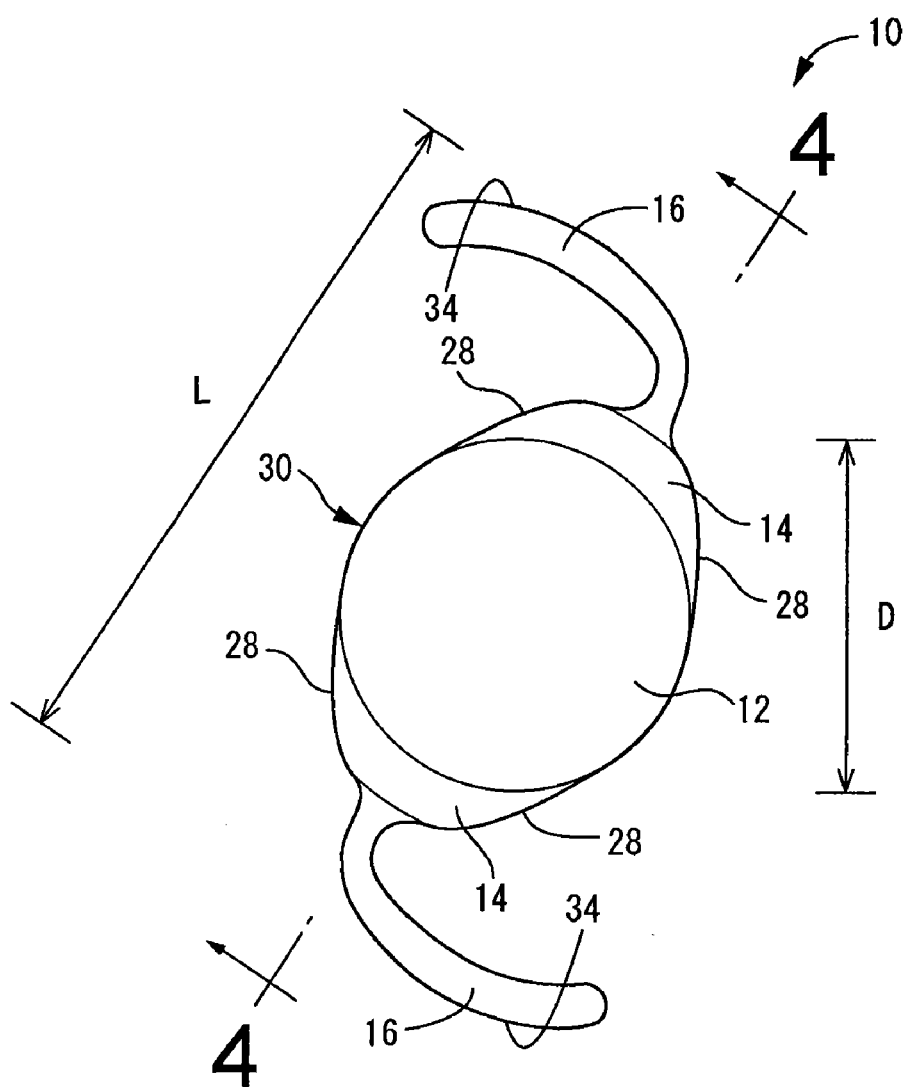
FIG. 1 is a front elevational view of an intraocular lens of one-piece type according to a first embodiment of the present invention.
Figure 2:
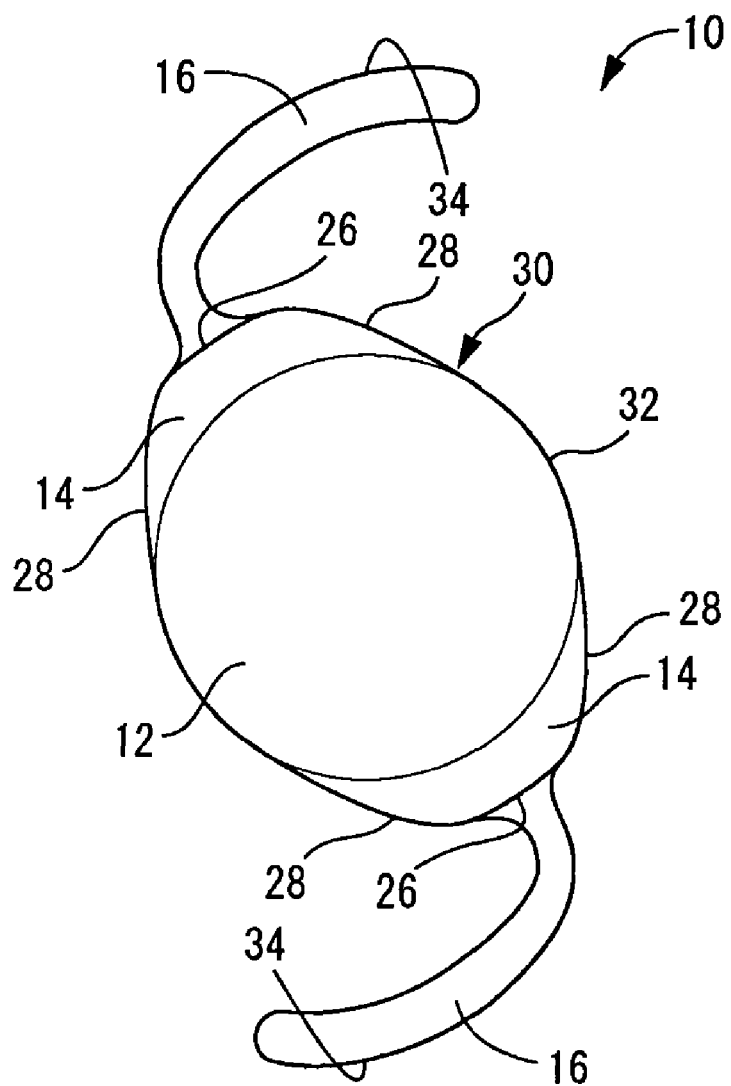
FIG. 2 is a rear elevational view of the intraocular lens of one-piece type of FIG. 1.
Figure 3:
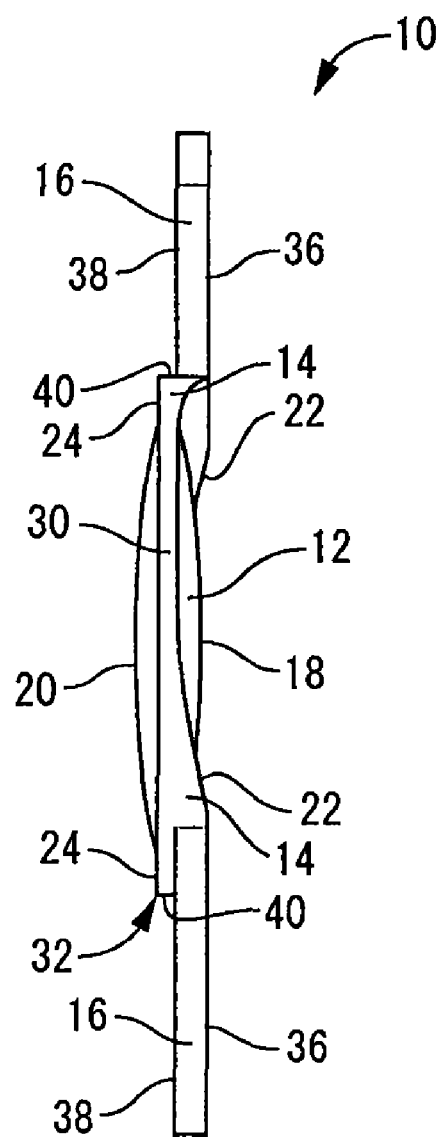
FIG. 3 is a side elevational view of the intraocular lens of one-piece type of FIG. 1.
Figure 4:
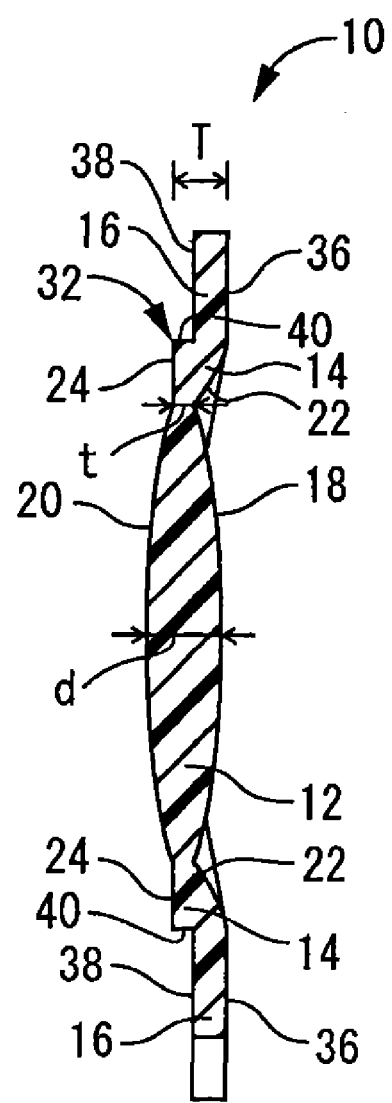
FIG. 4 is a vertical cross sectional view of the intraocular lens of one-piece type of FIG. 1, taken along line 4-4 of FIG. 1.

10 Intraocular lens
12 Optical portion
14 Coupling portions
16 Supporting portions
26 Arcuate outer circumferential surface
30 Outer circumferential wall surface
32 Continuous edge portion
40 Shoulder

BEST MODE FOR CARRYING OUT THE INVENTION

A fuller understanding of the present invention will be provided through the following detailed description of the embodiments, with reference to the accompanying drawings.

First, FIGS. 1 through 4 depict an intraocular lens 10 of foldable type, pertaining to a first embodiment of the present invention. This intraocular lens 10 includes an optical portion 12, a pair of coupling portions 14, 14, and a pair of supporting portions 16, 16.

This intraocular lens 10 having the optical portion 12, the coupling portions 14, 14, and the supporting portions 16, 16 may be formed of any of various materials endowed with visible light transmissivity sufficient to give an intraocular lens of foldable type, and endowed with excellent softness and certain amount of elasticity. In preferred practice, the soft material will have glass transition temperature of 30° C. or higher and refractive index of 1.51 or lower. Such soft materials enable the intraocular lens 10 to be easily folded or rolled up at normal temperature, so as to make it more compact as well as further facilitating insertion into the capsule during the implantation process.

Specifically, the materials taught in JP-A-10-24097 and JP-A 11-56998 are suitable for use as materials for forming the intraocular lens 10 pertaining to the present invention. Of these, monomers including one or more (meth)acrylic acid esters such as those listed in (i) below are preferred as they endow the intraocular lens with exceptional shape recovery. Optional suitable monomers such as those listed in (ii) below may be included also. Also, additives such as those listed in (iii) below may be added as needed.

(i) Included Monomers

Linear, branched, or cyclic alkyl (meth)acrylates such as the following:

methyl (meth)acrylate, ethyl (meth)acrylate, butyl (meth)acrylate, cyclohexyl (meth)acrylate, etc.

Hydroxyl group-containing (meth)acrylates such as the following:

hydroxyethyl (meth)acrylate, hydroxybutyl (meth)acrylate, diethylene glycol mono(meth)acrylate, etc.

Aromatic ring-containing (meth)acrylates such as the following:

phenoxyethyl (meth)acrylate, phenyl (meth)acrylate, phenyl ethyl (meth)acrylate, etc.

Silicone-containing (meth)acrylates such as the following:

trimethylsiloxy dimethylsilylmethyl (meth)acrylate, trimethylsiloxy dimethylsilylpropyl (meth)acrylate, etc.

Herein, the expression "(meth)acrylates" is used to refer collectively to "acrylates" and "methacrylates"; this convention will also be employed for other (meth)acrylic derivatives to be discussed later.

(ii) Optional Monomers (Meth)acrylamide and derivatives thereof such as the following:

(meth)acrylamide, N,N-dimethyl (meth)acrylamide, etc.

N-vinyl lactams such as the following:

N-vinyl pyrrolidone, etc.

styrene or derivatives crosslinking monomers such as the following:

butanediol di(meth)acrylate, ethylene glycol di(meth)acrylate (iii) Additives thermal polymerization initiators, photopolymerization initiators, photosensitizers, etc.

dyes etc.

UV absorbers etc.

During the process of integrally molding the illustrated intraocular lens 10 from these monomer materials, it is possible to use any of the various methods known in the conventional art. For example, the intended intraocular lens 10 could be obtained by a forming process involving cutting, or by a forming process involving molding. Where a cutting process is employed, prescribed polymer components selected from monomer materials such as the above will undergo polymerization to form a lens blank of appropriate shape such as a rod, block, or slab. The lens blank will then undergo a cutting process using a lathe or the like to produce the intraocular lens 10 of the desired shape. Where a molding process is employed, using a mold cavity that corresponds in shape to the intended shape of the intraocular lens 10, prescribed polymer components selected from monomer materials such as the above will be introduced into the mold cavity and subjected in situ to an appropriate polymerization procedure to obtain the intraocular lens 10 of the desired shape. The method of polymerization of the monomer material will be selected appropriately according to the particular monomer material, from among the various known methods such as thermal polymerization, photopolymerization, or some combination of these.

In the integrally formed intraocular lens 10 described above, the optical portion 12 is of generally disk shape which is circular in front view. The center portion of the optical portion 12 or the entire zone thereof constitutes a lens zone having optical properties that allow it to function as a substitute for the lens of the human eye. The lens surfaces of the optical portion 12 (the optical portion anterior surface 18 and the optical portion posterior surface 20) may take any of various shapes according to the required optical properties. The two surfaces 18, 20 are established by appropriate combination of concave surfaces, convex surfaces, planar surfaces, and so on. In the present embodiment, there is employed an optical portion 12 of convex lens shape, in which the optical portion anterior surface 18 and the optical portion posterior surface 20 are both spherical convex surfaces.

Here, the diameter dimension: D of the optical portion 12 is preferably within a range of 4.5-7.5 mm, more preferably 5.0-7.0 mm. However, the optical portion 12 must be of the size required for effective functioning as a substitute for the lens of the human eye. Additionally, since the size of the capsule of the human eye which will accommodate the intraocular lens 10 inserted therein is given, if the diameter dimension of the optical portion 12 should exceed 7.5 mm, the supporting portions 16, 16 will be too short and it will be difficult to achieve sufficient action in ameliorating outside force or a sufficient level of rearward displacement of the optical portion 12, as will be discussed later. There is also the risk of difficulty in sufficient compaction in size when folded or rolled during insertion into the eye.

The radial thickness dimension (thickness): d of the optical portion 12 in the direction of the optical axis (the lateral direction in FIG. 4) preferably has a maximum value of from 0.10 to 2.00 mm, more preferably a maximum value of from 0.20 to 1.50 mm. However, if the maximum value of the thickness dimension of the optical portion 12 is less than 0.1 mm, there is a risk that the optical portion will not exhibit consistent shape retention capability in the implanted state, whereas if the maximum value of the thickness dimension of the optical portion 12 exceeds 2.0 mm, it may be difficult in some instances to fold or roll the optical portion 12 to sufficiently small size during insertion into the capsule. In the present embodiment, the optical portion 12 is biconvex and has its maximum thickness dimension on an optical axis which is the geometric center. The specific value of the maximum thickness dimension: d will be established giving overall consideration to the characteristics (softness, refractive index, etc.) of the material being used, the shape and size of the optical portion 12, and so on.

The pair of coupling portions 14, 14 which extend a prescribed length in the circumferential direction are formed at the outer fringe part of the optical portion 12, projecting so as to be positioned at opposing locations along a direction lying across the diameter of the optical portion 12. Each coupling portion 14 is of generally trapezoidal shape in front view, gradually constricting in width in the circumferential on the projecting distal edge side.

The coupling portion 14 is composed of coupling portion anterior surfaces 22 constituted by sloping surfaces situated on one face in the direction of the optical axis (the optical portion anterior surface 18 side) and which, moving towards the outer fringe side, slope gradually towards the anterior surface side in the direction of the optical axis. Coupling portion posterior surfaces 24 situated on the other face are constituted by flat surfaces which extend perpendicular to the optical axis, so that moving towards the outer fringe side the coupling portion 14 as a whole increases gradually in thickness. Furthermore, the radial thickness dimension (thickness) at the inner fringe part of the coupling portion 14 in the direction of the optical axis is approximately the same as the radial thickness dimension (thickness) at the outer fringe part of the optical portion 12 in the direction of the optical axis. In the present embodiment, radial thickness of the outer fringe part of the optical portion 12 is substantially unchanging about the entire circumference of the optical portion 12. The radial thickness dimension (thickness) of the optical portion 12 outer fringe part in the direction of the optical axis is generally equal in those portions of the outer fringe part of the optical portion 12 where the coupling portions 14, 14 are formed and those portions where the coupling portions 14, 14 are not formed.

The outer circumferential surface of the coupling portion 14 is constituted as an arcuate outer circumferential surface 26 that projects towards the periphery and that serves as the arcuate distal end outer fringe part bowed so as to conform to the respective outside contour of the optical portion 12; while circumferential side wall faces 28, 28 that serve as the bilaterally disposed fringe portions situated to either edge of the coupling portion 14 in the circumferential direction are constituted by flat surfaces, whose edges lying towards the outer circumferential side connect smoothly with the arcuate outer circumferential surface 26 of the coupling portion 14, and whose edges lying towards the inner circumferential side connect smoothly with the outer circumferential face of the optical portion 12 without any inflection points or broken lines.

By means of this design, the outer circumferential faces of the coupling portions 14, 14 composed of the arcuate outer circumferential surface 26 and the circumferential side wall faces 28, 28 have smoothly curving surfaces, while the outer circumferential face of the optical portion 12 joins smoothly in the circumferential direction with the outer circumferential faces of the coupling portions 14, 14, whereby an outer circumferential wall surface 30 is constituted by the outer circumferential faces of the coupling portions 14, 14 and part of the outer circumferential face of the optical portion 12. The outer circumferential wall surface 30 extends in a direction generally parallel to the direction of the optical axis, and overall has a generally tubular shape extending in the direction of the optical axis. Smooth joining of these several surfaces refers to joining them without any inflection points or broken lines in the joined segments, so as to have a common tangent. In this instance in particular, the outer circumferential wall surface 30 as whole is constituted as a tubular bowed surface of varying curvature radius with a common tangent.

The outer circumferential wall surface 30 connects at its lower edge to the outer fringe parts of the optical portion posterior surface 20 and the coupling portion posterior surfaces 24. Thereby, an edge contour of an obtuse angle dependent on the convex shape of the optical portion posterior surface 20 is formed at the region of connection of the outer circumferential wall surface 30 with the optical portion posterior surface 20. An edge contour of an approximately right angle is formed at the region of connection of the outer circumferential wall surface 30 with the coupling portion posterior surfaces 24, forming a continuous edge portion 32 that creates an edge contour around the entire circumference of the connecting portion of the outer circumferential wall surface 30 and the posterior surfaces 20, 24.

The edge portion 32 has a shape extending smoothly and continuously around the entire circumference in the circumferential direction so as to surround the optical portion 12. In the present embodiment, the outer circumferential wall surface 30 is constituted about its entire circumference by outwardly convex bowed or flat surfaces. The edge portion 32 at the lower edge of the outer circumferential wall surface 30 extends continuously in the circumferential direction along an outer circumference gibbous curve which is convex towards the outside circumference about its entire circumference, and described by straight lines or curves. The coupling portion posterior surfaces 24 extend perpendicular to the optical axis from the outer fringe part of the optical portion posterior surface, whereby in the present embodiment the entire circumference of the edge portion 32 lies in the same plane extending perpendicular to the optical axis. The smoothly extending shape of the edge portion 32 refers to one described by connecting a function curve or a plurality of curves or straight lines (including all appropriate combinations thereof) in a manner devoid of inflection points or broken lines about the entire circumference. In the present embodiment in particular, connecting portions between the arcuate outer circumferential surface 26 and the circumferential side wall faces 28, 28, which are the portions with the smallest curvature radius in the circumferential direction in the edge portion 32, will preferably have a curvature radius of 0.3 mm or greater; more preferably curvature radius in these connecting portions will be 0.5 mm or greater, and still more preferably curvature radius in these connecting portions will be 1.0 mm or greater.

The pair of supporting portions 16, 16, meanwhile, are formed on each arcuate outer circumferential surface 26 of the coupling portions 14, 14. The pair of supporting portions 16, 16 have thin, elongated rod shape, and are respectively projected outwardly in the diametrical direction of the optical portion 12 from the circumferential central portions of the arcuate outer circumferential surfaces 26, 26, as well as extending in bowed configuration along the circumferential direction of the optical portion 12. The outer circumferential side faces of the bowed portions of the pair of supporting portions 16, 16 constitute contact surfaces 34, 34 for disposition in contact against the inside surface of the capsule in the eye with the intraocular lens 10 inserted into the capsule. By means of this design, in the present embodiment, the optical portion 12 is supported positioned at the prescribed location within the capsule by means of the pair of supporting portions 16, 16.

The distance L: separating the contact surfaces 34, 34 of the pair of supporting portions 16, 16 situated in opposition will preferably be between 10 and 15 mm, and more preferably between 10.5 and 14.5 mm, established in consideration of the diameter dimension of the optical portion 12. The lens will thereby be adapted to the size of the capsule of the typical human eye, making it possible for the intraocular lens 10, including the optical portion 12, to be advantageously positioned within the capsule.

The radial thickness dimension (thickness) of the supporting portions 16, 16 is smaller than the radial thickness dimension of the coupling portions 14, 14 at their outer circumferential edge. In the present embodiment, radial thickness is also slightly greater than radial thickness in the outer fringe part of the optical portion 12. The supporting portions 16, 16 extend from the edge of the outer circumferential end face of the coupling portions 14, 14, on the coupling portion anterior surfaces 22 thereof. That is, within a plane extending perpendicular to the optical axis, a pair of supporting portion anterior surfaces 36, 36 which constitute the surfaces on a first side of the supporting portions 16, 16 in the direction of the optical axis are positioned generally co-planar with the outer circumferential edge of the pair of coupling portion anterior surfaces 22; while the pair of supporting portion posterior surfaces 38, 38 situated on the other side of the supporting portions 16, 16 in the direction of the optical axis are positioned biased further towards the anterior surface side than are the pair of coupling portion posterior surfaces 24, 24. By means of this arrangement, a shoulder 40 is formed between the supporting portion posterior surfaces 38 and the coupling portion posterior surfaces 24, thereby forming part of the edge portion 32 at the lower edge of the shoulders 40 in the direction of the optical axis. Moreover, the center point of the supporting portions 16, 16 in their thickness direction (direction of the optical axis) is positioned further towards the anterior surface side than the center point of the optical portion 12 in its thickness direction (direction of the optical axis). In the present embodiment in particular, the supporting portions 16, 16 which extend perpendicular to the optical axis are situated further towards the anterior surface side in the direction of the optical axis, than is the outer fringe part of the optical portion 12.

The intraocular lens 10 having the structure discussed above, in its entirety including the optical portion 12 and the supporting portions 16, 16, can be folded or rolled in the appropriate direction to reduce its overall size. Then, following known procedures, an incision is made in part of the eye, the lens is removed from the site using suction etc., and the intraocular lens 10 reduced to small size is inserted through the incision wound and into the capsule. An appropriate insertion instrument may be used for the insertion operation if needed.

In the present embodiment in particular, the intraocular lens 10 can be folded or rolled (this includes curling, rolling, etc.) in a direction generally orthogonal to the direction of opposition of the pair of supporting portions 16, 16 about an axis extending in the direction of opposition of the pair of supporting portions 16, 16, in order to produce an overall shape that is elongated in the direction of projection of the supporting portions 16, 16 which will advantageously reduce the size of the intraocular lens 10. Specifically, in the present embodiment, while the pair of coupling portions 14, 14 are projected in one direction across the diameter of the optical portion 12 from which the pair of supporting portions 16, 16 are projected, no such coupling portions 14, 14 that project towards the outer periphery of the optical portion 12 are present in the aforementioned folding or rolling direction, and small size can be maintained. For this reason, despite the presence of the coupling portions 14, 14, the profile area towards the direction of projection of the pair of supporting portions 16, 16 (which is also the direction of insertion) can be reduced to a sufficient extent by folding or rolling, making it possible to keep the incision wound small during insertion into the capsule.

The intraocular lens 10 which has now been implanted so as to be accommodated in its entirety within the capsule will expand within the capsule so as to recover its initial shape based on its elasticity. Optionally, an appropriate instrument may be used to adjust the position of the intraocular lens 10 within the capsule, thereby positioning the intraocular lens 10 within the capsule so as to align the optical axis of the intraocular lens 10 with the opthalmologic center axis of the eye. With the intraocular lens 10 in the implanted state, since the distance: L between the contact surfaces 34, 34 of the two supporting portions 16, 16 in the intraocular lens 10 is designed to be greater than the inside diameter dimension of the capsule, the contact surfaces 34, 34 of the two supporting portions 16, 16 will come into intimate contact against the inside surface at the outer periphery of the capsule, thereby positioning and immobilizing the optical portion 12 within the eye.

Here, the optical portion 12 and the coupling portions 14 of the intraocular lens 10 are disposed with their posterior surfaces 20, 24 in contact with the inside surface of the capsule and with the edge portion 32 formed on the outer fringe part of the posterior surfaces 20, 24 pressed into intimate contact against the inside surface of the capsule. The inside surface of the capsule, by means of being pressed by the edge portion 32, undergoes bending deformation in conformance with the contour of the edge at the location of contact of the edge portion 32 against the inside surface of the capsule. In the present embodiment in particular, the edge portion 32 is formed by smooth curving lines or straight lines around the entire circumference in the circumferential direction. Since the edge portion is formed over a continuous path in the circumferential direction so as to extend along a smooth curve with no inflection points, concentration of stress at a particular location can be avoided in the edge portion 32 despite the fact that it presses against the capsule inside surface with a relatively high level of force, and a consistent level of pressing force can be exerted around the entire circumference.

In the one-piece intraocular lens 10 of structure according to the present embodiment, the outer circumferential surfaces of the optical portion 12 and the coupling portions 14, 14 are integrally formed by the smooth outer circumferential wall surface 30 which is devoid of any corners. The edge portion 32 is formed by this outer circumferential wall surface 30 and the posterior surfaces 20, 24, whereby the edge portion 32 is formed so as to extend smoothly and continuously around the entire circumference. For this reason, wrinkling or other such irregular deformation of the contour of the capsule inside surface can be more advantageously prevented, as compared with a conventional intraocular lens formed with an edge portion that has a corner (inflection point) along part of its circumference. By maintaining the posterior surfaces 20, 24 of the optical portion 12 and the coupling portions 14, 14 in stable intimate contact against the capsule inside surface, migration of epithelial cells into the optical zone can be prevented and the onset of secondary cataracts can be effectively inhibited.

In particular, where as in the intraocular lens 10 of the present embodiment, the pair of coupling portions 14, 14 are formed at circumferential sections of the optical portion 12 and project out along one direction across the diameter thereof, it will be possible nevertheless to attain a sufficient level of intimate contact of the edge portion 32 against the capsule inside surface, by means of smoothly joining the optical portion 12 outer circumferential surface with the side wall surfaces of the coupling portions 14, 14.

Moreover, in the present embodiment, the optical axis-direction radial thickness dimension: T at the outer fringe part of the coupling portion 14 is greater than the optical axis-direction radial thickness dimension: t at the inner fringe part of the coupling portion 14. For this reason, the optical axis-direction dimensions of the supporting portions 16, 16 and the shoulders 40, 40 can be more advantageously assured, as compared with the case where the pair of supporting portions 16, 16 of smaller thickness dimension than the outer fringe part of the optical portion 12 project out through direct extension from the outer fringe of the optical portion 12. Accordingly, adequate strength of the supporting portions 16, 16 can be assured, sufficient height of the shoulders 40, 40 can be assured, and the effect of intimate contact afforded by pressing of the edge portion 32 against the capsule inside surface can be attained effectively. In the present embodiment in particular, in order to avoid optical distortion and the like in the optical portion 12, portions of the outer fringe part of the optical portion 12 in which the coupling portions 14, 14 are formed are not made especially thick, but rather formed with a thickness dimension generally equal to that of portions in which the coupling portions 14, 14 are absent, so that the outer fringe part of the optical portion 12 has generally unchanging thickness dimension about its entire circumference. Even where such a shape has been adopted for the optical portion 12, by giving the coupling portions 14, 14 a shape that is thicker at the outer circumferential side, and coupling the supporting portions 16, 16 to the optical portion 12 via these coupling portions 14, 14, it will be possible to advantageously ensure adequate thickness of the supporting portions 16, 16 without being influenced substantially by the thickness dimension of the outer fringe part of the optical portion 12 which has been established according to the required optical properties.

Moreover, in the present embodiment, the coupling portion anterior surfaces 22, 22 are constituted by sloping faces that slope gradually towards the anterior surface side in the direction of the optical axis moving towards the outside in the direction perpendicular to the optical axis. The supporting portions 16, 16 are formed so as to extend out from the distal edge on the outside circumferential surface of the coupling portions 14, 14, on the coupling portion anterior surface 22, 22 side thereof. For this reason, with the intraocular lens 10 implanted in the capsule, the optical portion 12 and the coupling portions 14, 14 readily undergo displacement towards the posterior surface side in the direction of the optical axis, by means of contact reaction force acting on the supporting portions 16, 16. Accordingly, the optical portion 12 and the coupling portions 14, 14 will be guided to into displacement towards the posterior surface side in the direction of the optical axis, whereby the edge portion 32 will be advantageously pressed against the capsule inside surface, and a condition of intimate contact against the capsule inside surface will be advantageously achieved.

Furthermore, in the present embodiment, the outer circumferential surface of the coupling portion 14 is outwardly convex in the direction perpendicular to the optical axis. Thus, the edge portion 32 is disposed in stable contact about its entire circumference against the spherical bowing contour of the inside surface of the capsule, and stress or strain caused by contact will be dispersed over a wide area of the capsule inside surface, thereby advantageously achieving a state of intimate contact with no gap between the edge portion 32 and the inside surface of the capsule.

Moreover, in the present embodiment, the edge portion 32 is formed so as to extending over the coupling portion posterior surfaces 24 which lie in a given plane extending in the generally perpendicular direction to the optical axis. The edge portion 32 can therefore be disposed in intimate contact against the spherical bowing contour of the inside surface of the capsule with a generally uniform condition of contact therewith about the entire circumference, thus more effectively avoiding concentrated action of stress.

Furthermore, in the present embodiment, the pair of supporting portions 16, 16 have identical and unchanging thickness dimensions, with the thickness dimension of the supporting portions 16, 16 being greater than the thickness dimension at the outer fringe part of the optical portion 12. For this reason, with the intraocular lens 10 inserted within the capsule, the contact surfaces 34, 34 of the supporting portions 16, 16 will be disposed in contact against the inside surface of the capsule. Despite the action of contact reaction force produced by contact of the supporting portions 16, 16 against of the capsule, concentration of stress will not readily occur in the segments of appreciable change in width dimension in the circumferential direction, namely, the connecting segments between the coupling portions 14, 14, and the supporting portions 16, 16, and thus buckling and other irregular deformation can be advantageously prevented from occurring in the basal end portion of the supporting portions 16, 16. Accordingly, failure of the intraocular lens 10 can be effectively prevented, and contact reaction force can be transmitted efficiently to the edge portion 32 via the supporting portions 16, 16, so that adequate pressing force can be consistently attained.

Moreover, in the present embodiment, by coupling the optical portion 12 and the supporting portions 16, 16 through the agency of the coupling portions 14, 14 which are wider in shape in the circumferential direction than are the supporting portions 16, 16, the contact reaction force transmitted by the supporting portions 16, 16 can be dispersed and/or cushioned by the coupling portions 14, 14, thereby advantageously preventing contact reaction force from becoming concentrated at particular locations in the optical portion 12. For this reason, distortion in the optical portion 12 caused by the action of contact reaction force can be avoided, and astigmatism or other disruptions of optical properties in association with such distortion can be effectively prevented.

Furthermore, in the present embodiment, the outer circumferential surfaces of both the optical portion 12 and the coupling portions 14, 14 are bowing surfaces that extend in the direction of the optical axis. The outer circumferential wall surface 30 constituted by these outer circumferential surfaces of the optical portion 12 and the coupling portions 14 is an optical axis-direction surface that extends generally parallel to the optical axis. For this reason, it is possible to advantageously form the angle of the edge portion 32 that is formed by the outer circumferential wall surface 30, the optical portion posterior surfaces 20, and the coupling portion posterior surfaces 24.

Moreover, in the present embodiment, the arcuate outer circumferential surfaces 26, 26 of the coupling portions 14, 14 are disposed in a generally concentric circular arrangement that bows along the outer circumferential surface of the optical portion 12, and thus in the event that the intraocular lens 10 is formed by means of a cutting process (lase cutting method), it will be easier to control operation during cutting, making it possible to execute a highly accurate cutting process; or where formed by means of a molding process, it will be possible to reduce or avoid internal stress and residual strain.

Figure 5:
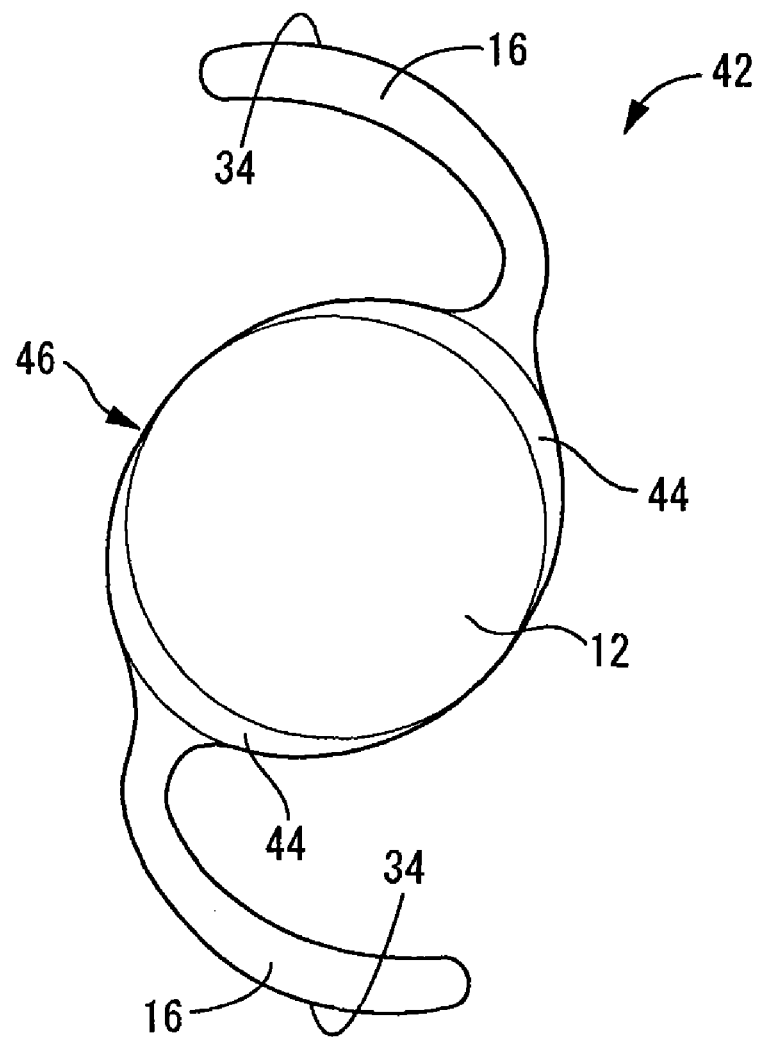
FIG. 5 is a front elevational view of an intraocular lens of one-piece type according to a second embodiment of the present invention.
Figure 6:
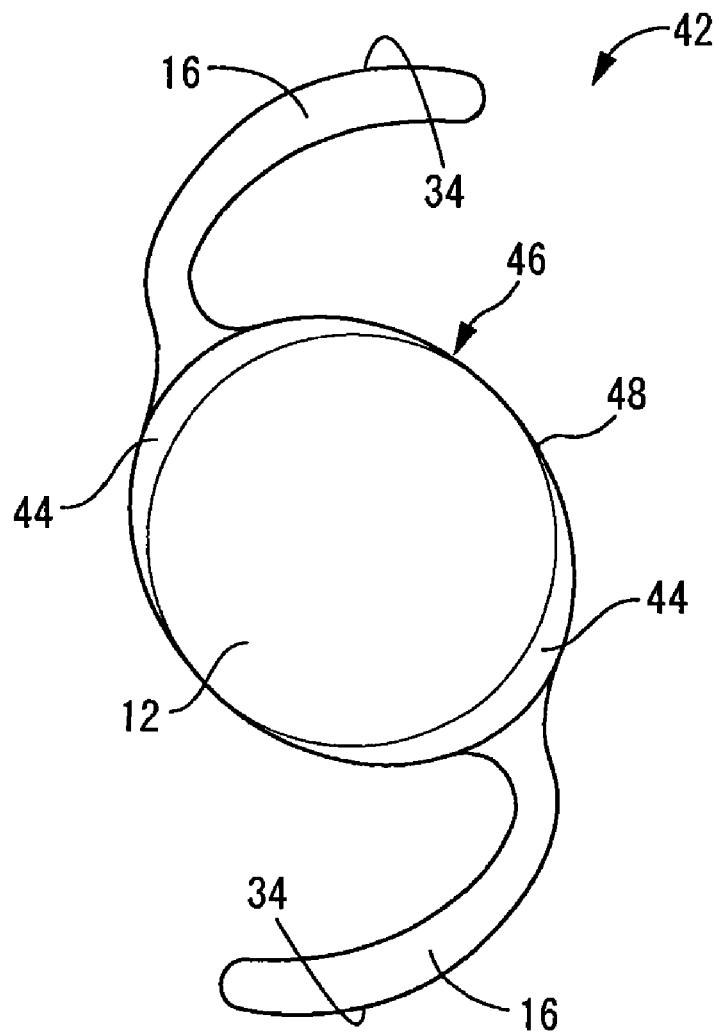
FIG. 6 is a rear elevational view of the intraocular lens of one-piece type of FIG. 5.
Figure 7:
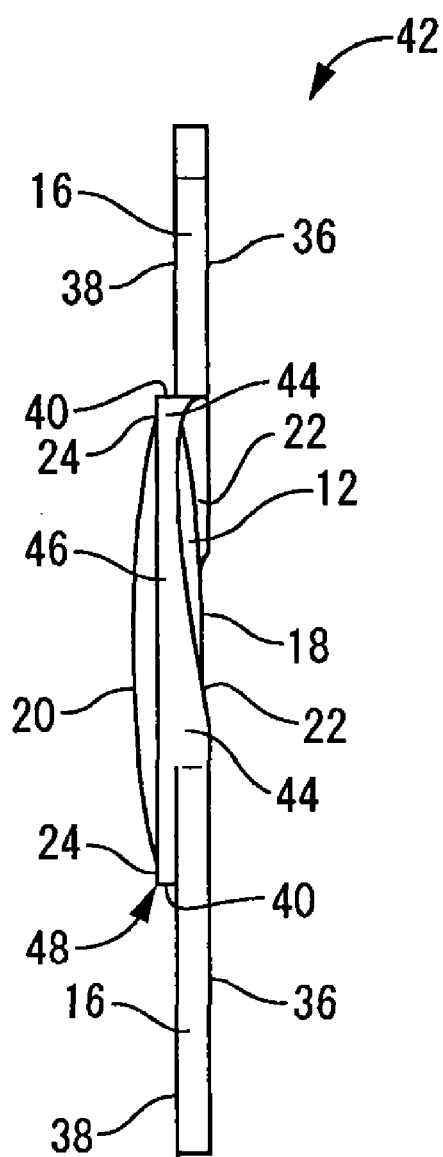
FIG. 7 is a side elevational view of the intraocular lens of one-piece type of FIG. 5.

Next, an intraocular lens 42 of foldable type pertaining to a second embodiment of the present invention will be described with reference to FIGS. 5, 6, and 7. In the following description, parts and areas that are substantially identical to those in the preceding first embodiment will be assigned identical symbols in the drawing and will not be discussed in any detail.

Specifically, the intraocular lens 42 pertaining to the present embodiment is integrally formed of any of various soft materials such as those mentioned in the preceding first embodiment. The inner fringe of the coupling portions 44, 44 has a generally semicircular shape in front view, while the outer fringe has a generally semi-elliptical shape in front view, so that their inner fringe and outer fringe meet at each of their respective ends in the circumferential direction. That is, in the present embodiment, the pair of coupling portions 44, 44 of generally crescent moon shape in front view are disposed in opposition to either side of the optical portion 12 in one direction across the diameter of the optical portion 12.

The outside circumferential surface of the optical portion 12 and the outside circumferential surface of the coupling portions 44, 44 join together smoothly in the circumferential direction, and their outside circumferential surfaces together constitute an outer circumferential wall surface 46 in the present embodiment. In front view, this outer circumferential wall surface 46 is of generally tubular shape having generally elliptical shape along the outer circumferential contours of the pair of coupling portions 44, 44. An edge portion 48 is formed in the segment where the lower edge part of the outer circumferential wall surface 46 meets the outer fringe parts of the posterior surfaces 20, 24 of the optical portion 12 and the coupling portions 44, 44. The edge portion 48 in the present embodiment extends continuously in the circumferential direction so as to constitute a generally elliptical shape in rear view, and is formed so as to extend over a smooth curve with no inflection points about the entire circumference. In the present embodiment, as will be apparent from the fact that the edge portion 48 describes a generally elliptical shape in rear view, the edge portion 48 is an outer circumference gibbous curve which is convex towards the outer circumference about its entire circumference.

The intraocular lens 42 of structure according to the present embodiment affords effects similar to those of the first embodiment discussed previously. In particular, the generally elliptical shape in front view of the coupling portions 44, 44 as taught in the intraocular lens 42 of the present embodiment affords stable contact about the entire circumference against the spherical bowed contour of the capsule inside surface, thereby more advantageously dispersing stress and strain on the capsule, and improving intimate contact.

While the present invention has been described herein through certain preferred embodiments, the invention should not be construed as limited in any way to the specific disclosures in those embodiments.

Figure 8:
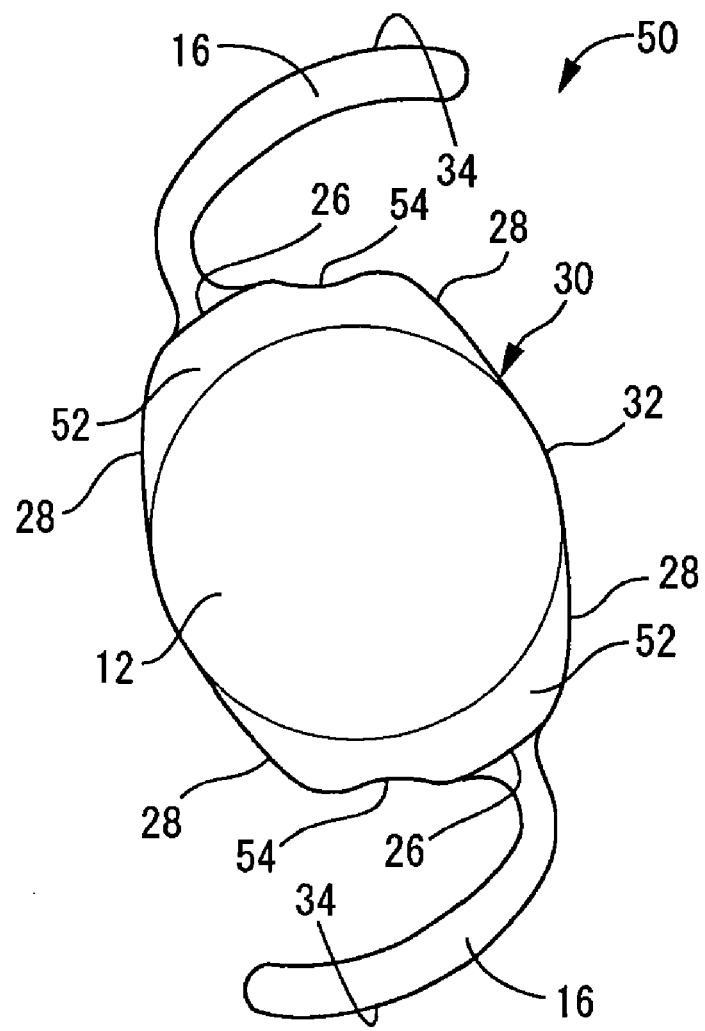
FIG. 8 is a rear elevational view of an intraocular lens of one-piece type according to a third embodiment of the present invention.

For example, the shape of the coupling portions is in no way limited to that taught specifically in the first and second embodiments. Specifically, FIG. 8 depicts an intraocular lens 50 pertaining to a third embodiment of the present invention, for example. In the intraocular lens 50 pertaining to the present embodiment, the coupling portion 52 is generally rectangular in shape in front view, with a recessed part 54 of generally recessed shape towards the outer circumferential side formed in a portion of the outer circumferential surface of the coupling portion 52. This intraocular lens 50 affords effects identical to those of the intraocular lenses 10, 42 in the first and second embodiments.

In particular, in the intraocular lens 50 of the present embodiment, the recessed part 54 formed in each of the pair of coupling portions 52, 52, reduces the thickness dimension of the coupling portions 52, 52 in the direction of opposition of the recessed parts 54, 54. For this reason, even where the coupling portions 52, 52 are thicker than the outer fringe part of the optical portion 12, the intraocular lens 50 can be folded easily about an axis extending in the direction of opposition of the recessed parts 54, 54, thus advantageously allowing the intraocular lens 50 to be made compact in size through folding or rolling during insertion into the capsule. Furthermore, where the intraocular lens 50 is to be positioned in a specific insertion tool and inserted into the eye by being pushed in with a plunger, since the concave recessed parts 54, 54 are formed on the coupling portions 52, 52, by positioning the distal end of the plunger in abutment against the recessed parts 54, 54 of the coupling portions 52, 52 to push in the lens, it can be easily positioned in the direction perpendicular to the optical axis. For this reason, in instances where the intraocular lens 50 is to be pushed into the eye, the force needed to position it in the optical axis-perpendicular direction can be kept to a minimum, facilitating the insertion operation. Moreover, by forming the recessed parts 54, 54 in opposition to one another in a direction across the diameter of the optical portion 12, the centering or other aligning operations carried out after the intraocular lens 50 has been inserted into the eye can be accomplished easily and with a high degree of accuracy.

Figure 9:
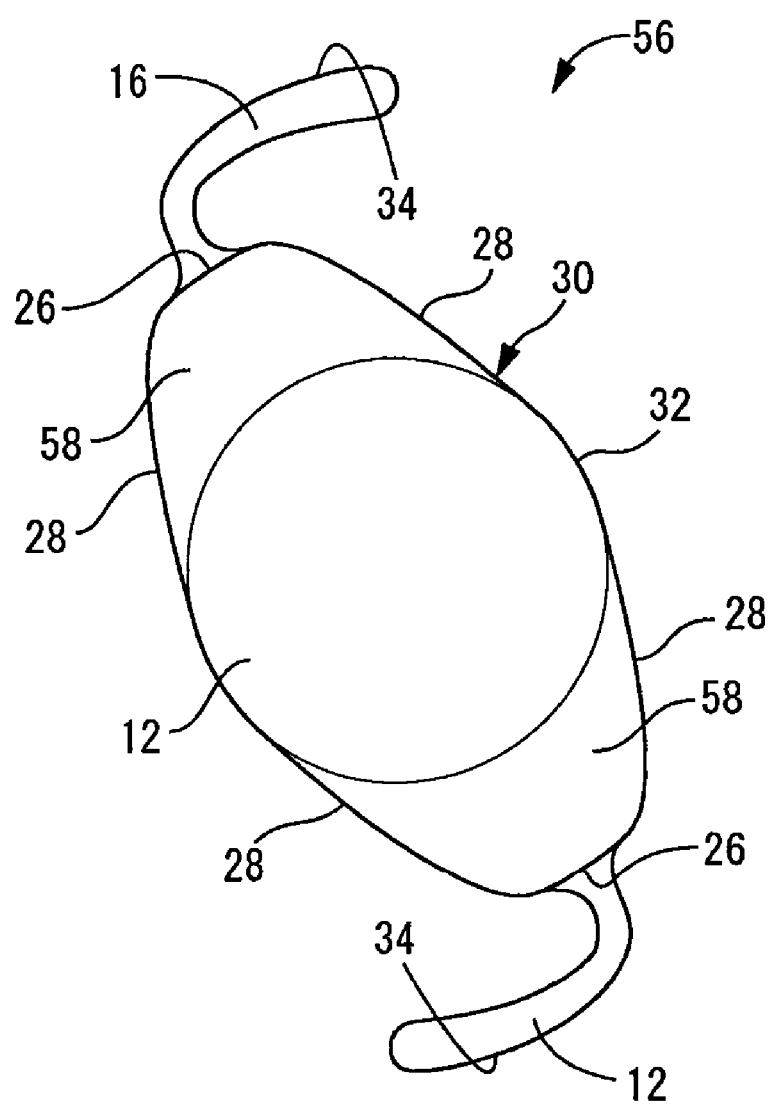
FIG. 9 is a rear elevational view of an intraocular lens of one-piece type according to a fourth embodiment of the present invention.

Furthermore, the projected length of the coupling portion 14 (44) in the direction of projection of the pair of coupling portions 14, 14 (44, 44) can be established appropriately. Specifically, FIG. 9 depicts an intraocular lens 56 pertaining to a fourth embodiment of the present invention, for example. In the intraocular lens 56 pertaining to the present embodiment, the projected length of the coupling portion 58 from the outer fringe of the optical portion 12 is longer in comparison with the intraocular lens 10 of the first embodiment illustrated in FIGS. 1 through 4. The profile area of the coupling portion 58 in the direction of the optical axis is larger. With this intraocular lens 56, the edge portion 32 will be able to contact the capsule inside surface over a wider area, thus more advantageously dispersing stress and strain.

Figure 10:
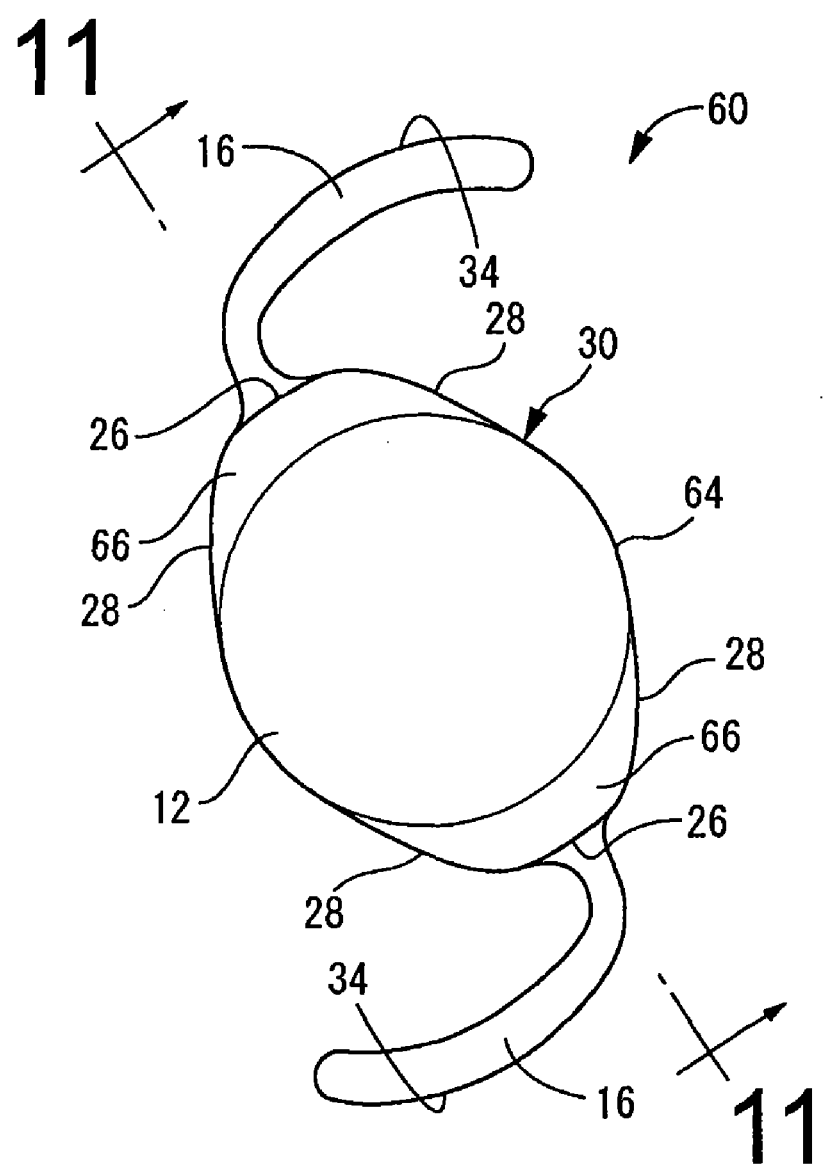
FIG. 10 is a rear elevational view of an intraocular lens of one-piece type according to a fifth embodiment of the present invention.
Figure 11:
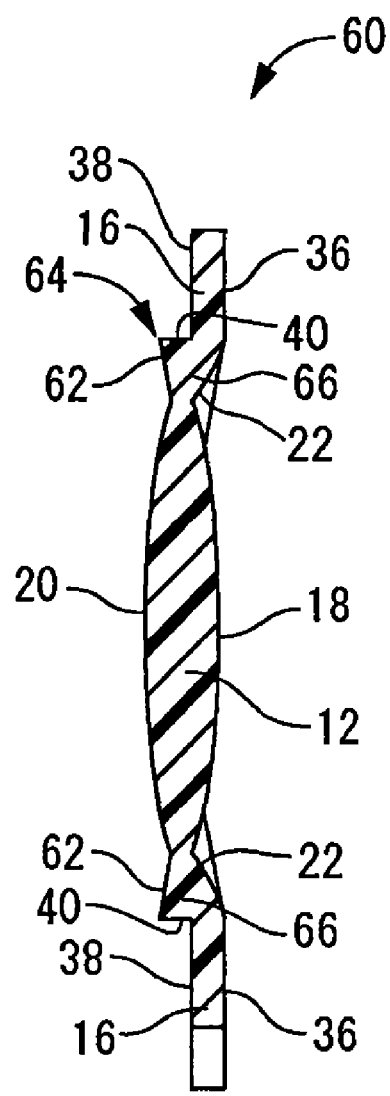
FIG. 11 is a vertical cross sectional view of the intraocular lens of one-piece type of FIG. 10, taken along line 11-11 of FIG. 10.

While the preceding first and second embodiments described examples in which the angle of the edge portion 32 is approximately 90 degrees, the angle of the edge portion may be set as appropriate. Specifically, FIGS. 10 and 11 depict an intraocular lens 60 pertaining to a fifth embodiment of the present invention, for example. In the intraocular lens 60 pertaining to the present embodiment, the outer circumferential wall surface 30 has a generally tubular shape extending in the direction of the optical axis, and the coupling portion posterior surface 62 is constituted by a sloping surface that moving outwardly in the diametrical direction slopes towards the posterior surface side, thus giving the edge portion 64 an angle of less than 90 degrees. By imparting the edge portion 64 with an acute angle in this way, the thickness dimension at the outer fringe part of the coupling portion 66 in the present embodiment can be advantageously assured. With the intraocular lens 60 implanted in the capsule, the edge portion 64 can be disposed in more solid intimate contact against the inside surface of the capsule, thus advantageously preventing infiltration of epithelial cells into the optical zone. In the present embodiment in particular, by making the slope angle of the coupling portion posterior surface 62 smaller than the slope angle of the coupling portion anterior surface 22, sufficient radial thickness of the supporting portions 16, 16 and sufficient height of the shoulders 40 can be ensured without an appreciable degree of bias of the location of the edge portion 64 in the direction of the optical axis towards the posterior surface side in comparison with the optical portion posterior surface 20. For this reason, the optical portion posterior surface 20 can be disposed in sufficiently intimate contact against the posterior capsule while at the same time achieving the effect of inhibiting migration of epithelial cells by the edge portion 64, thus advantageously affording a lower incidence of secondary cataracts.

The shape of the supporting portion 16 is in no way limited to that taught specifically in the first and second embodiments. Specifically, supporting portions of various shapes like those illustrated in FIGS. 12 through 17 could be employed, for example.

Figure 12:
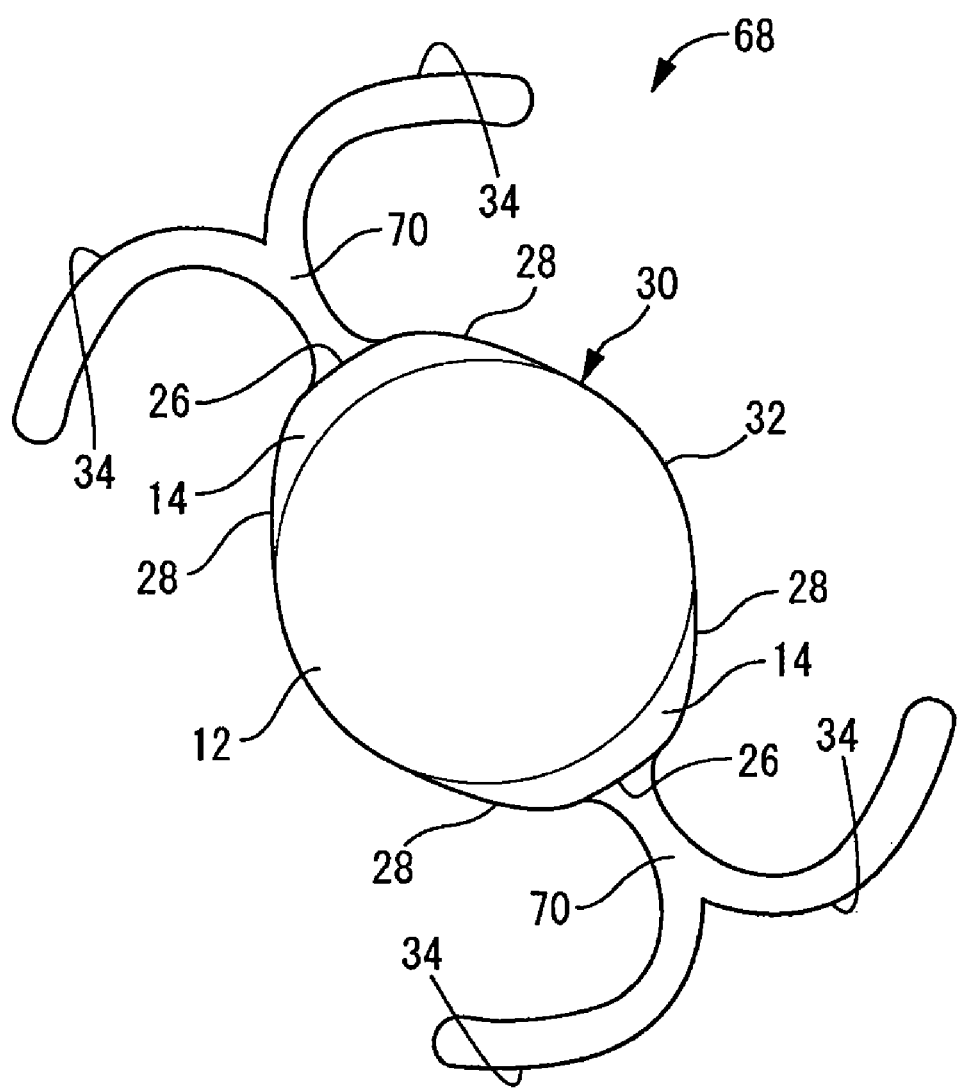
FIG. 12 is a rear elevational view of an intraocular lens of one-piece type according to a sixth embodiment of the present invention.

Specifically, FIG. 12 depicts an intraocular lens 68 pertaining to a sixth embodiment of the present invention. In the intraocular lens 68 pertaining to the present embodiment, the supporting portion 70 in a medial section thereof branches into two forks, with the portions lying further towards the projecting distal end from this medial section respectively bowing along the circumferential direction of the optical portion 12 and extending in mutually opposite directions. The intraocular lens 68 having the supporting portion 70 of this design affords greater stability of the optical portion 12 and more secure support when inserted into the capsule.

Figure 13:
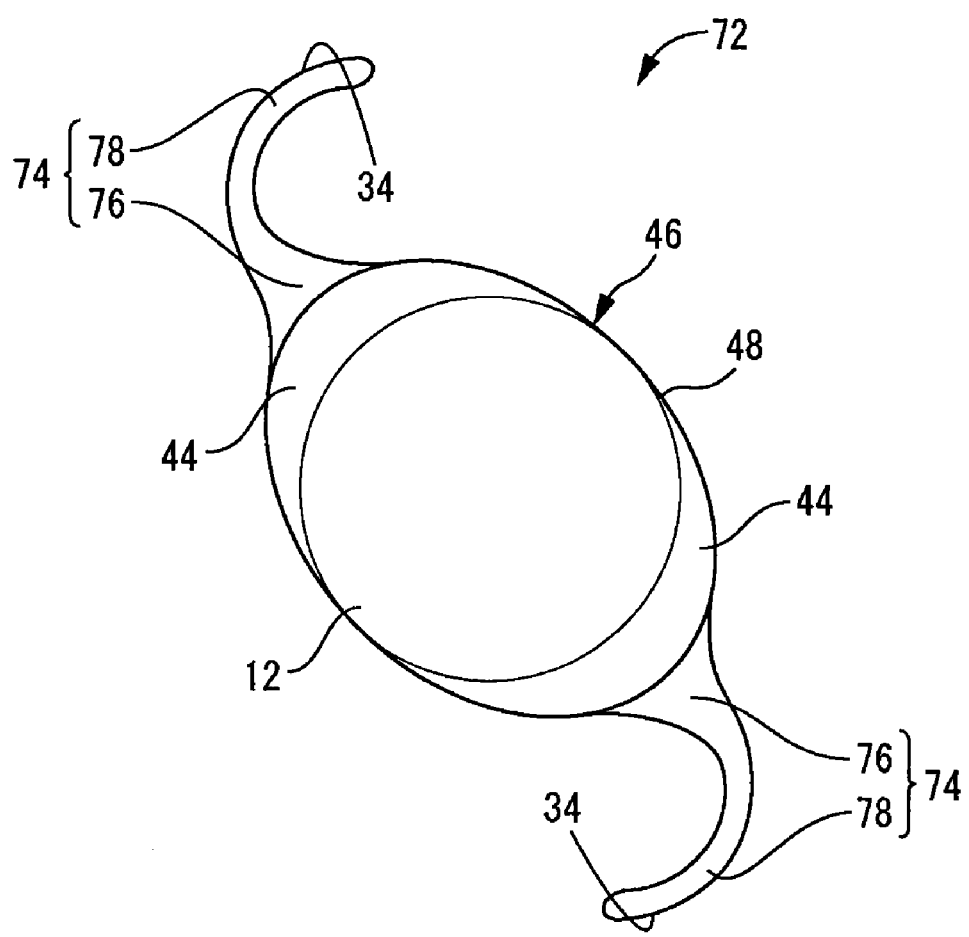
FIG. 13 is a rear elevational view of an intraocular lens of one-piece type according to a seventh embodiment of the present invention.

FIG. 13 depicts an intraocular lens 72 pertaining to a seventh embodiment of the present invention. In the intraocular lens 72 pertaining to the present embodiment, the basal end portion 76 of the supporting portion 74, i.e. the side thereof that connects with the outer circumferential surface of the coupling portion 14, is wider in shape than its projecting distal end portion 78. The projecting distal end portion 78 is bowed along the circumferential direction of the optical portion 12. The intraocular lens 72 having the supporting portion 74 of this design can ensure sufficient rigidity by means of the relatively wide basal end portion 76; affords stable positioning and immobilization of the optical portion 12 at the prescribed location; affords a sufficient level of pliability owing to the relatively thin projecting distal end portion 78; and can prevent injury to capsule caused by the supporting portion 74 coming into contact with the inside surface of the capsule, as well as avoiding damage to the intraocular lens 72 by contact reaction force.

Figure 14:
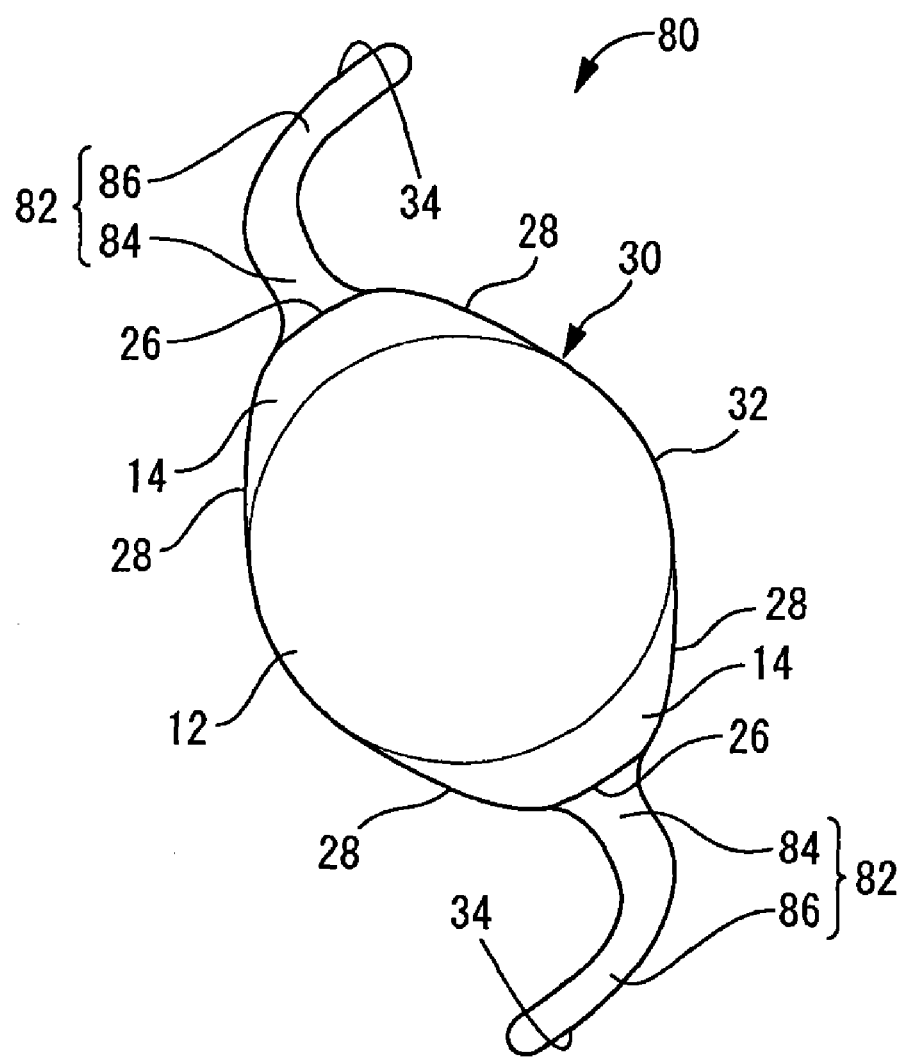
FIG. 14 is a rear elevational view of an intraocular lens of one-piece type according to an eighth embodiment of the present invention.

FIG. 14 depicts an intraocular lens 80 pertaining to an eighth embodiment of the present invention. In the intraocular lens 80 pertaining to the present embodiment, the supporting portion 82 extends in a generally linear rod configuration that bends in the optical axis-perpendicular direction in its medial section, with its basal end portion 84 situated towards the coupling portion 14 from this medial section being wider in shape relative to its projecting distal end portion 86. The intraocular lens 80 having the supporting portion 82 of this design affords effects similar to the preceding seventh embodiment, as well as affording stronger mating of the projecting distal end of the supporting portion 82 against the inside surface of the capsule.

Figure 15:
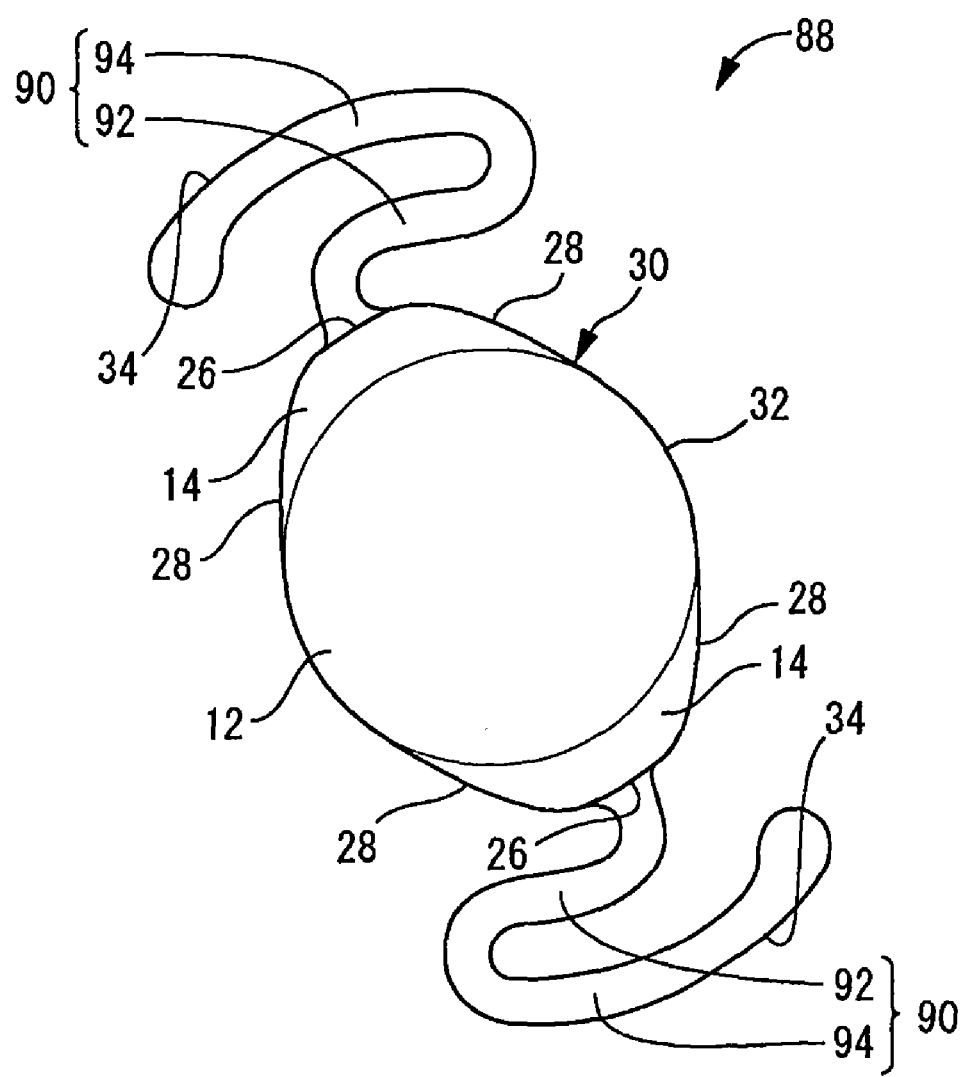
FIG. 15 is a rear elevational view of an intraocular lens of one-piece type according to a ninth embodiment of the present invention.

FIG. 15 depicts an intraocular lens 88 pertaining to a ninth embodiment of the present invention. In the intraocular lens 88 pertaining to the present embodiment, the supporting portion 90 as a whole is bent into a generally hooked configuration. In more detail, the pair of supporting portions 90, 90 are situated in opposition along one direction across the diameter of the optical portion 12 and project outwardly in the diametrical direction with the supporting portions bent or bowed in the medial section, forming a pair of medial portions 92, 92 that extend a given length along the circumferential direction of the optical portion 12 and that extend in mutually opposite directions in the circumferential direction. The medial portions 92, 92 are further bent or bowed in sections thereof to form distal end portions 94, 94 that extend in mutually opposite directions in the circumferential direction. In the present embodiment, the medial portions 92 and the distal end portions 94 extend in a generally concentric circular arrangement, with the distal end portions 94 having greater radius of curvature than the medial portions 92. The intraocular lens 88 having the supporting portion 90 of this design, by virtue of the hook configuration produced by a hairpin bend, can advantageously cushion stress acting on the capsule due to contact when the intraocular lens in implanted in the inside surface of the capsule, thus avoiding the problem of injury to the capsule.

Figure 16:
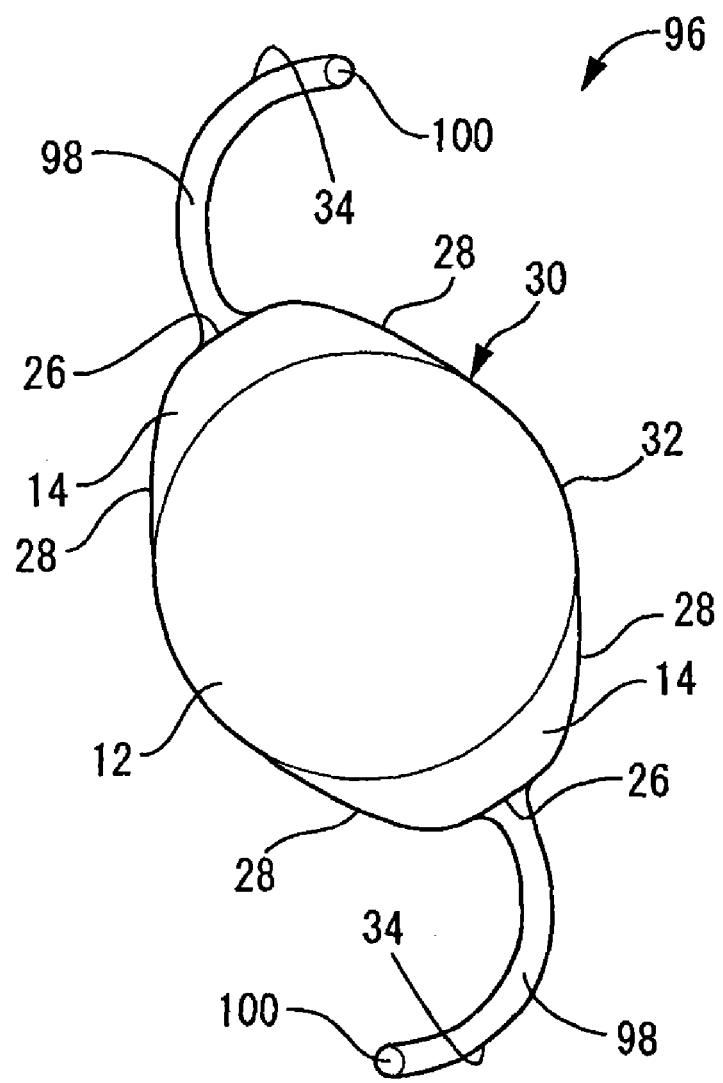
FIG. 16 is a rear elevational view of an intraocular lens of one-piece type according to a tenth embodiment of the present invention.
Figure 17:
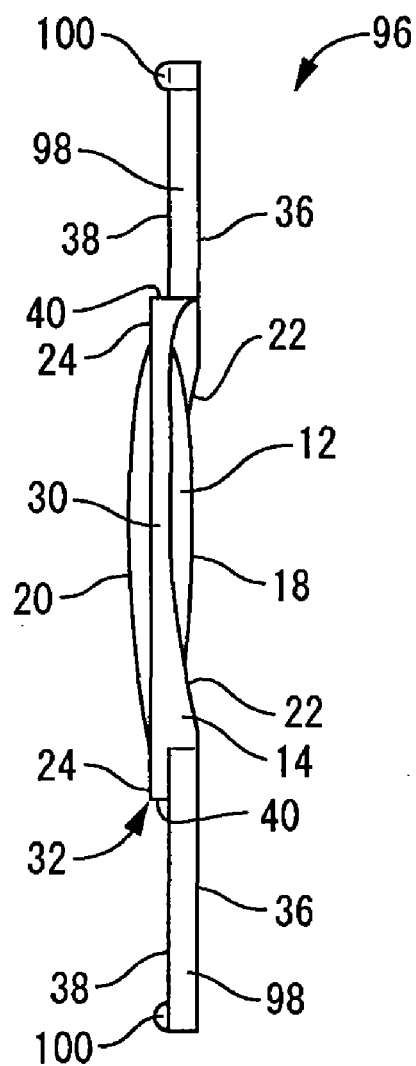
FIG. 17 is a side elevational view of the intraocular lens of one-piece type of FIG. 16.

FIGS. 16 and 17 depict an intraocular lens 96 pertaining to a tenth embodiment of the present invention. In the intraocular lens 96 pertaining to the present embodiment, the supporting portion 98 as a whole is of thin, elongated rod shape extending in an arcuate shape with generally unchanging width; and has a projection 100 projecting from the supporting portion posterior surface 38 at its projecting distal end. The supporting portion 98 of this design makes it possible to prevent advantageously the drawback that, due to the presence of the projection 100 formed on the supporting portion posterior surface 38, the distal end of the supporting portion 98 will adhere to another area against which it is juxtaposed when the intraocular lens 96 is folded for insertion into the capsule. After insertion the supporting portion 98 will recover its initial shape, thereby more reliably positioning and immobilizing the optical portion 12 in the prescribed position.

Figure 18:
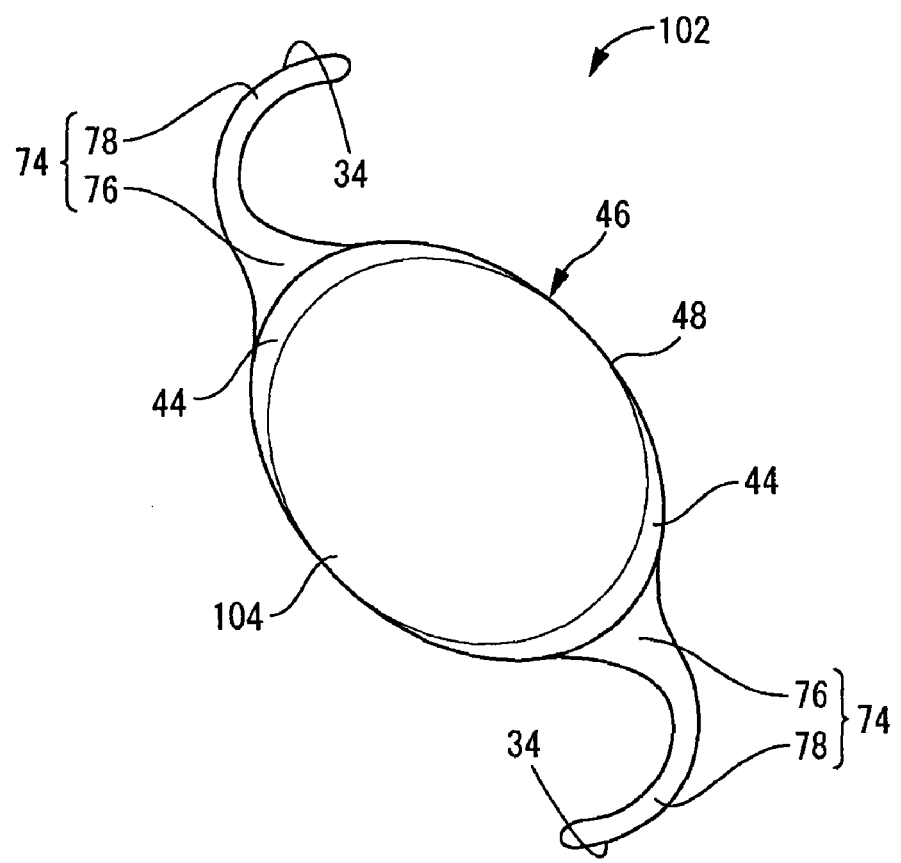
FIG. 18 is a rear elevational view of an intraocular lens of one-piece type according to an eleventh embodiment of the present invention.

In order to advantageously avoid optical distortion and the like in the optical portion 12, the optical portion 12 will preferably be circular in front view as described in the first and second embodiments. However, the optical portion 12 need not necessarily be circular in front view. As a specific example, it could instead have a generally elliptical shape in plan view like that of the optical portion 104 in the intraocular lens 102 shown in FIG. 18 by way of an eleventh embodiment.

Figure 19:
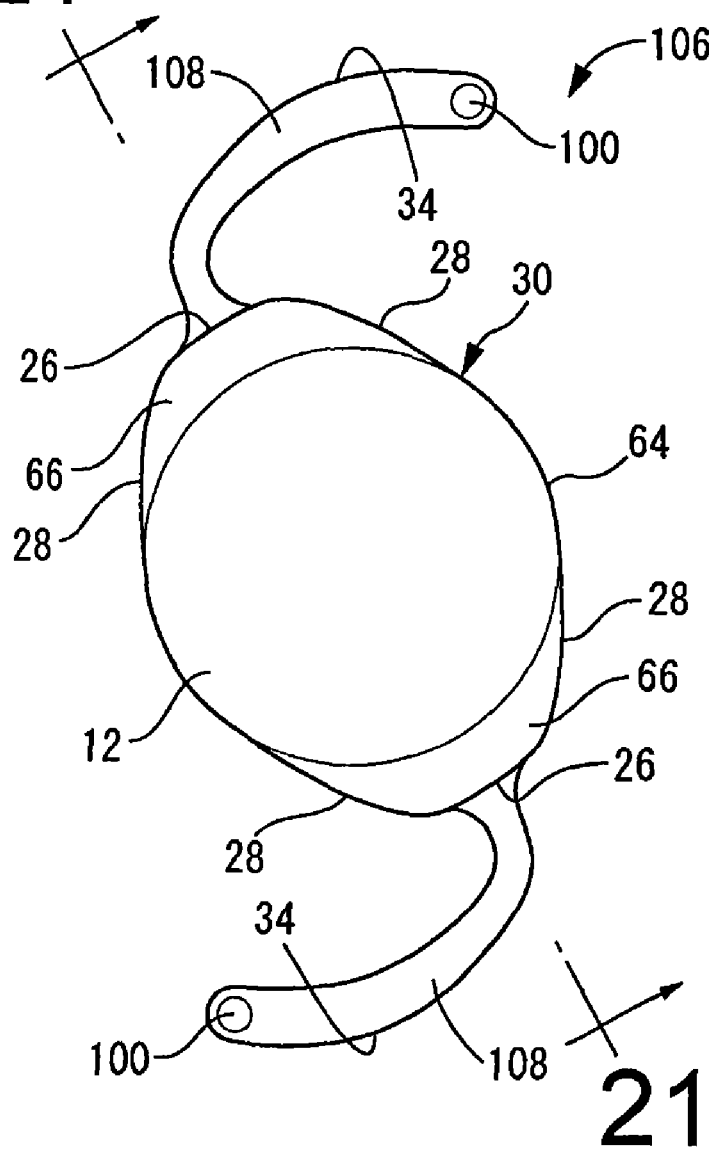
FIG. 19 is a rear elevational view of an intraocular lens of one-piece type according to a twelfth embodiment of the present invention.
Figure 20:
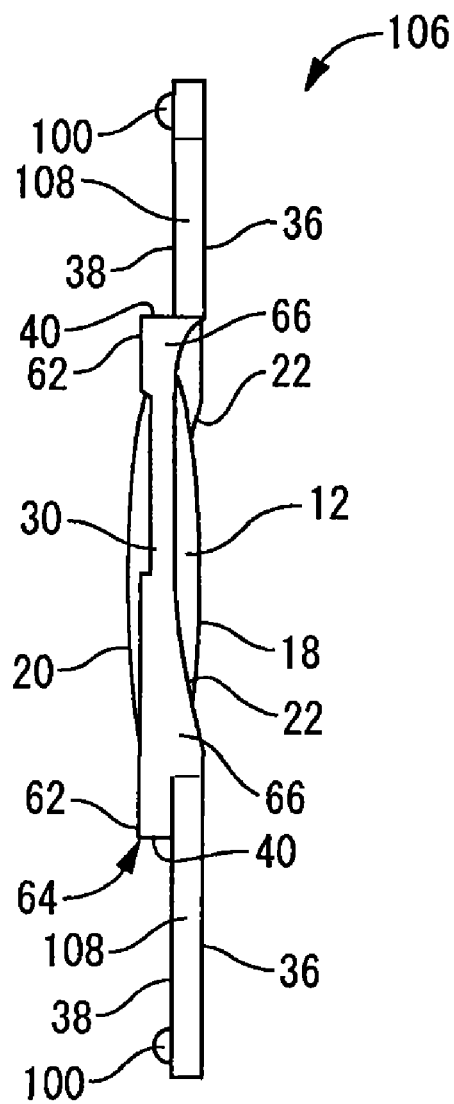
FIG. 20 is a side elevational view of the intraocular lens of one-piece type of FIG. 19.
Figure 21:
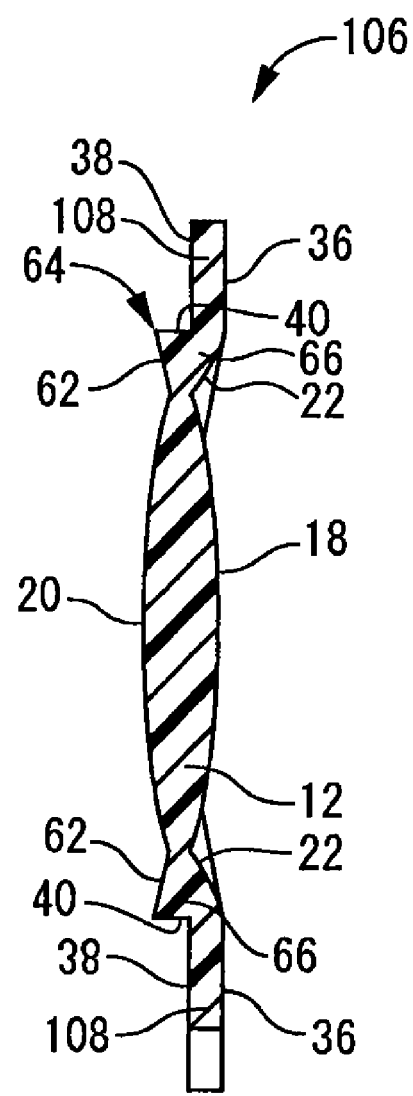
FIG. 21 is a cross sectional view of the intraocular lens of one-piece type of FIG. 19, taken along line 21-21 of FIG. 19.

The various regions and parts described in the first through eleventh embodiments may of course be combined in any appropriate manner to produce intraocular lenses. A specific example is the intraocular lens 106 shown in FIGS. 19 through 21 by way of a twelfth embodiment of the present invention. The intraocular lens 106 pertaining to the present embodiment is provided with the acute-angle edge portion 64 shown in the previous fifth embodiment. The supporting portions 108 are provided at their distal end with the projections 100 shown in the previous tenth embodiment.

Figure 22:
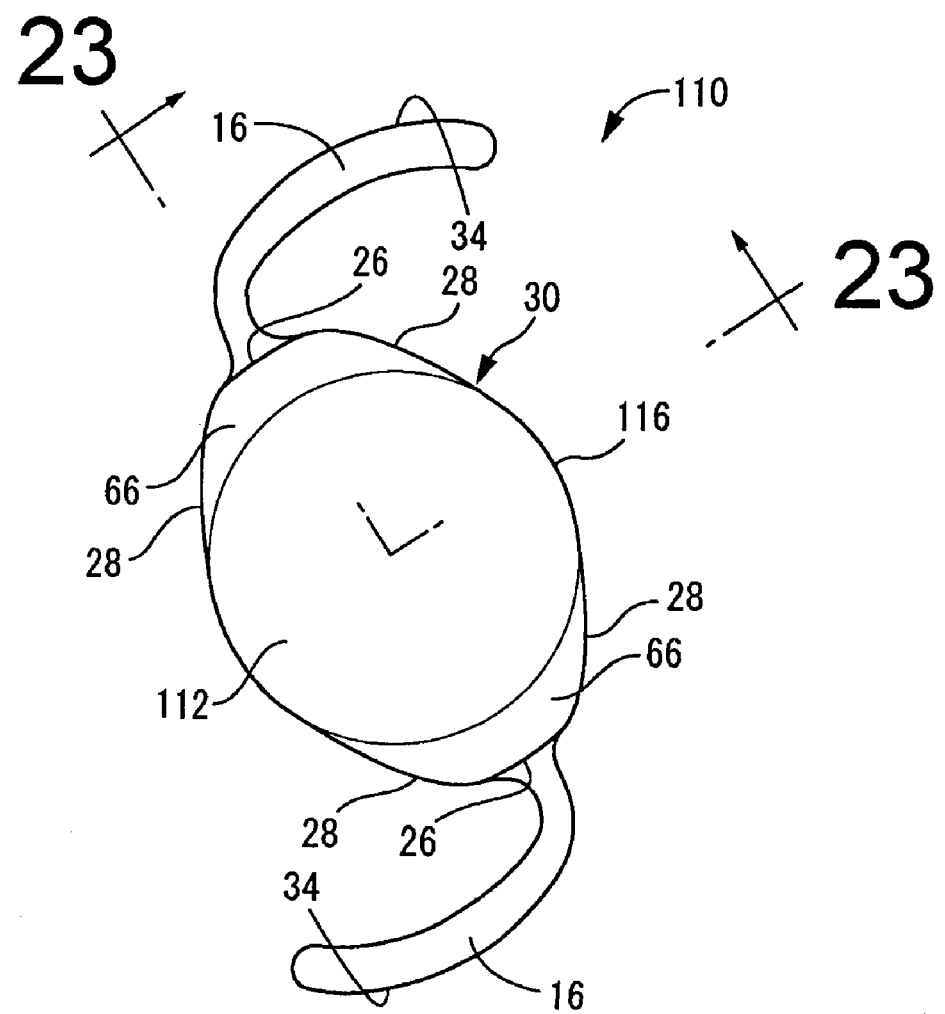
FIG. 22 is a rear elevational view of an intraocular lens of one-piece type according to a thirteenth embodiment of the present invention.
Figure 23:
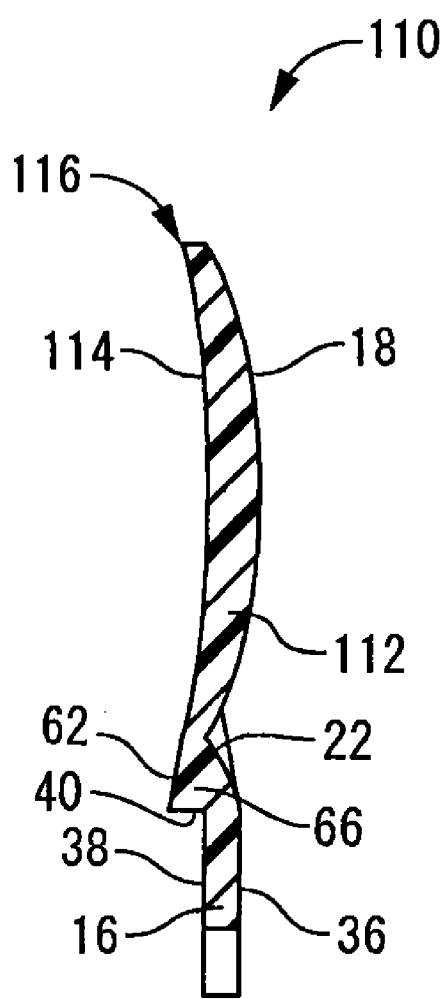
FIG. 23 is a cross sectional view of the intraocular lens of one-piece type of FIG. 22, taken along line 23-23 of FIG. 22.

FIGS. 22 and 23 depict an intraocular lens 110 pertaining to a thirteenth embodiment of the present invention. In the intraocular lens 110 pertaining to the present embodiment, the outer circumferential wall surface 30 has a tubular shape extending generally parallel to the direction of the optical axis. The coupling portion posterior surfaces 62, 62 are constituted by sloping surfaces which, moving diametrically outward, are sloped towards the posterior surface side, while the optical portion posterior surface 114 of the optical portion 112 is concave in shape, whereby the edge portion 116 is imparted with an acute angle about its entire circumference. In the intraocular lens 110 of structure according to the present embodiment, contact of the edge portion 116 against the posterior capsule can be advantageously achieved, and infiltration of epithelial cells into the optical zone can be prevented. In particular, in the present embodiment, the optical portion anterior surface 18 of the optical portion 112 is of gibbous shape having greater curvature than the optical portion posterior surface 114.

Moreover, as with the supporting portions 74, 82 shown in the preceding seventh and eighth embodiments, the width dimension of the supporting portion may vary between its basal end and distal end. Thickness dimension of the supporting portion, i.e. its dimension in the direction of the optical axis, may be established appropriately depending on characteristics such as the strength required of the supporting portion, and so on. As a specific example, the supporting portion may become gradually thinner towards its projecting distal end. By employing such a supporting portion it will be possible to lower strength at the projecting distal end portion so as to reduce reaction force during contact, while at the same time ensuring adequate strength at the basal end portion, to attain sufficient positioning action of the intraocular lens by the supporting portions.

In the first through thirteenth embodiments, the outer circumferential wall surfaces 30, 46 are formed so as to extend generally parallel to the direction of the optical axis, and in association therewith, the outer circumferential surface of the optical portion 12 and the outer circumferential surfaces of the coupling portions 14, 44, 52, 58 which together constitute the outer circumferential wall surfaces 30, 46 are all constituted by curving surfaces that extend parallel to the direction of the optical axis. However, the outer circumferential wall surfaces 30, 46, and hence the outer circumferential surfaces of the optical portion 12 and the coupling portions 14, 44, 52, 58, need not be formed so as to extend parallel to the direction of the optical axis. As a specific example, by constituting the outer circumferential wall surface as a sloping surface whose anterior surface side in the direction of the optical axis slopes gradually outward in the optical axis-perpendicular direction, it would be possible to improve strength in the connecting section that connects the supporting portion with the coupling portion. Furthermore, by constituting the outer circumferential wall surface as a sloping surface whose anterior surface side in the direction of the optical axis slopes gradually inward in the optical axis-perpendicular direction, the edge portion cross section can be easily given an edge angle which is an acute angle, thus improving intimate contact against the inside surface of the capsule.

The edge portions 32, 48, 64 may be formed so as to extend substantially smoothly in the circumferential direction; or may include obtuse angles approximating 180 degrees.

In order to reduce concentration of stress at the connecting sections of the supporting portions 16, 70, 74, 82, 90, 98, 108 and the coupling portions 14, 44, 52, 58, 66, as shown in the first through thirteenth embodiments, in preferred practice wide parts with rounded contours will be disposed to either side in the width direction at the basal end side of the supporting portions 16, 70, 74, 82, 90, 98, 108, so as to gradually increase in width towards the connecting sections thereof with the coupling portions 14, 44, 52, 58, 66. However, such rounded wide parts need not necessarily be provided at the basal end side of the supporting portions 16, 70, 74, 82, 90, 98, 108.

While not given individually herein, the present invention may be reduced to practice in various other modes incorporating variations, modifications and improvements which would be apparent to those skilled in the art, and these embodiments will of course fall within the scope of the invention insofar as they do not depart from the spirit thereof.

The invention claimed is:

1. An intraocular lens of one-piece type comprising:

an optical portion of generally circular shape in front view and including a lens zone having prescribed optical characteristics integrally formed with supporting portions that extend radially outwardly from the optical portion, the lens being configured to be inserted in an eye, and disposed to be in contact against an inside surface of an outer circumferential part of a capsule thereby holding the optical portion positioned pressed against the inside surface of the capsule on a retinal side thereof;

an edge contour of edge shape extending smoothly along an entire circumference of the optical portion in a circumferential direction, the edge contour located on a posterior side of the intraocular lens, the edge contour configured to be pressed against the inside surface of the retinal side of the capsule, and the edge contour comprising an outer circumferential surface including a shoulder that constitutes an axial surface that is generally parallel to the center axis of the optical portion and extends continuously around the entire circumference of the optical portion so as to surround the optical portion; and a pair of coupling portions, which respectively spread outwardly in a diametrical direction from the outer circumferential part of the optical portion at locations situated in opposition along one direction across a diameter of the optical portion, are formed with circumferential length greater than the supporting portions, each coupling portion including an anterior surface and a posterior surface, wherein the supporting portions are formed projecting out from outer fringe parts of the coupling portions, with a thickness dimension at each outer fringe part of the coupling portion from which the supporting portion projects out being greater than a thickness dimension at an outer fringe part of the optical portion, wherein at the outer fringe part of the coupling portion in a coupling section thereof with the supporting portion, the coupling portion projects further in a posterior direction than the supporting portion so that the outer fringe parts of the optical portion and the posterior surfaces of the pair of coupling portions cooperate to form the edge contour, wherein a pair of supporting portion anterior surfaces, which constitute surfaces on an anterior side of the supporting portions in the direction of the optical axis, are positioned generally co-planar with an outer circumferential edge of the pair of coupling portion anterior surfaces, the supporting portion anterior surfaces extending further in an anterior direction of the intraocular lens than any other part of the intraocular lens, wherein a pair of supporting portion posterior surfaces, which constitute surfaces on a posterior side of the supporting portions in the direction of the optical axis, are positioned biased further towards the anterior surface side than are the pair of coupling portion posterior surfaces, wherein the shoulder is formed between the supporting portion posterior surfaces and the coupling portion posterior surfaces, wherein the supporting portions are formed so as to extend out from distal edges on outside circumferential surfaces of the coupling portions on the anterior surface side, which is biased towards an anterior surface of the optical portion, and wherein the anterior surfaces of the coupling portions are sloping surfaces which are sloped further anterior going outwardly away from the optical portion, the posterior surfaces of the coupling portions are sloping surfaces which are sloped further posterior going outwardly away from the optical portion, the anterior surfaces of the coupling portions have a larger slope angle than the posterior surfaces of the coupling portions, and the supporting portion anterior surfaces extend further in an anterior direction of the intraocular lens than any other part of the intraocular lens in an anterior region corresponding to the edge contour located on the posterior side of the intraocular lens.

2. The intraocular lens according to claim 1, wherein the edge contour along the entire circumference thereof in the circumferential direction is either linear or gibbous-curving towards an outside circumference.

3. The intraocular lens according to claim 1, wherein the edge contour about the entire circumference thereof is positioned in a given plane extending generally orthogonal to a center axis of the optical portion.

4. The intraocular lens according to claim 1, wherein the posterior surfaces of the coupling portions are generally flat surfaces extending in a generally orthogonal direction to the center axis of the optical portion.

5. The intraocular lens according to claim 1, wherein a thickness dimension at a basal portion of the supporting portions projecting out from the coupling portions is equal to or greater than a thickness dimension at locations away from portions where the coupling portions are formed at the outer fringe part of the optical portion.

6. The intraocular lens according to claim 1, wherein a thickness dimension of the outer fringe part of the optical portion is generally unchanging along the entire circumference, including those areas where the coupling portions are formed and other areas away from those areas where the coupling portions are formed.

7. The intraocular lens according to claim 1, wherein the edge contour has an acute angle cross section in at least a portion thereof.

8. The intraocular lens according to claim 1, wherein the outer fringe part of the coupling portion is composed of an arcuate distal end outer fringe part with an outer circumferential face of arcuate shape disposed concentrically with the center axis of the optical portion, and bilaterally disposed fringe portions for smoothly connecting respective circumferential edge portions of the arcuate distal end fringe part to the outer fringe part of the optical portion; and wherein a width dimension of the supporting portions is smaller than the circumferential length of the arcuate distal end fringe part, with the supporting portion formed projecting from a circumferential center portion of the arcuate distal end fringe part.

9. The intraocular lens according to claim 1, wherein each of the pair of supporting portions projects extending out in a direction generally orthogonal to the center axis of the optical portion; and a center point of the supporting portion in a thickness direction thereof is positioned with bias towards the anterior surface of the optical portion, in relation to a center point of the thickness direction of the optical portion.

10. The intraocular lens according to claim 1, wherein the lens is integrally formed of soft material that is foldable or rollable.

11. The intraocular lens according to claim 1, wherein each of the coupling portions extends along only a portion of the circumference of the optical portion.

12. The intraocular lens according to claim 1, wherein the pair of supporting portions are respectively projected outwardly in the diametrical direction of the optical portion from the circumferential central portions of the outer fringe part of the coupling portion.

13. The intraocular lens according to claim 1, wherein the edge contour has a pair of outermost surfaces with respect to the optical portion that orthogonally and respectively connect to the pair of supporting portion posterior surfaces.

14. An intraocular lens of one-piece type comprising:
an optical portion of generally circular shape in front view and including a lens zone having prescribed optical characteristics integrally formed with supporting portions that extend radially outwardly from the optical portion, the lens being configured to be inserted in an eye, and disposed to be in contact against an inside surface of an outer circumferential part of a capsule thereby holding the optical portion positioned pressed against the inside surface of the capsule on a retinal side thereof;
an edge contour of edge shape extending smoothly along an entire circumference of the optical portion in a circumferential direction, the edge contour located on a posterior side of the intraocular lens, the edge contour configured to be pressed against the inside surface of the retinal side of the capsule, and the edge contour comprising an outer circumferential surface including a shoulder that constitutes an axial surface that is generally parallel to the center axis of the optical portion and extends continuously around the entire circumference of the optical portion so as to surround the optical portion; and
a pair of coupling portions, which respectively spread outwardly in a diametrical direction from the outer circumferential part of the optical portion at locations situated in opposition along one direction across a diameter of the optical portion, are formed with circumferential length greater than the supporting portions, each coupling portion including an anterior surface and a posterior surface,
wherein the supporting portions are formed projecting out from outer fringe parts of the coupling portions, with a thickness dimension at each outer fringe part of the coupling portion from which the supporting portion projects out being greater than a thickness dimension at an outer fringe part of the optical portion,
wherein at the outer fringe part of the coupling portion in a coupling section thereof with the supporting portion, the coupling portion projects further in a posterior direction than the supporting portion so that the outer fringe parts of the optical portion and the posterior surfaces of the pair of coupling portions cooperate to form the edge contour,
wherein a pair of supporting portion anterior surfaces, which constitute surfaces on an anterior side of the supporting portions in the direction of the optical axis, are positioned generally co-planar with an outer circumferential edge of the pair of coupling portion anterior surfaces, the supporting portion anterior surfaces extending further in an anterior direction of the intraocular lens than any other part of the intraocular lens,
wherein a pair of supporting portion posterior surfaces, which constitute surfaces on a posterior side of the supporting portions in the direction of the optical axis, are positioned biased further towards the anterior surface side than are the pair of coupling portion posterior surfaces,
wherein the shoulder is formed between the supporting portion posterior surfaces and the coupling portion posterior surfaces,
wherein the supporting portions are formed so as to extend out from distal edges on outside circumferential surfaces of the coupling portions on the anterior surface side, which is biased towards an anterior surface of the optical portion, and
wherein a posterior-most edge of the edge contour about the entire circumference of the posterior face of the optical portion is flat and is positioned within a given plane extending generally orthogonally to the optical axis of the optical portion.

15. The intraocular lens according to claim 14, wherein an anterior-most edge of the edge contour about the entire circumference of an anterior face of the optical portion contains slopes.

* * * * *